United States Patent [19]

Weier et al.

[11] Patent Number: 5,262,426
[45] Date of Patent: Nov. 16, 1993

[54] N,N'-CYCLOALKYL/ALKYL CARBOXAMIDE 4H-IMIDAZO-[4,5-B]PYRIDINE COMPOUNDS AS PAF ANTAGONISTS

[75] Inventors: Richard M. Weier, Lake Bluff; Ish K. Khanna, Vernon Hills; Michael A. Stealey, Libertyville; Janet A. Julien, Glenview, all of Ill.

[73] Assignee: G. D. Searle & Co., Chicago, Ill.

[21] Appl. No.: 7,461

[22] Filed: Jan. 22, 1993

[51] Int. Cl.$^5$ .................. A61K 31/435; C07D 471/04
[52] U.S. Cl. ..................... 514/303; 514/63; 514/234.2; 514/255; 544/127; 544/362; 544/405; 546/14; 546/118
[58] Field of Search ............... 546/118, 14; 544/127, 544/362, 405; 514/63, 234.2, 255, 303

[56] References Cited

U.S. PATENT DOCUMENTS

| | | |
|---|---|---|
| 2,987,518 | 6/1961 | Hoffman et al. |
| 4,003,908 | 1/1977 | Denzel et al. ............ 260/295.5 |
| 4,243,671 | 1/1981 | Harris et al. ............ 424/273 |
| 4,284,641 | 8/1981 | Thorogood ............ 424/273 |
| 4,357,340 | 11/1982 | Thorogood ............ 424/273 |
| 4,416,895 | 11/1983 | Thorogood ............ 424/273 |
| 4,579,862 | 4/1986 | Manley et al. ............ 514/399 |
| 4,804,658 | 2/1989 | Manley et al. ............ 514/234.2 |
| 4,914,108 | 4/1990 | Khanna et al. ............ 514/303 |

FOREIGN PATENT DOCUMENTS

| | | |
|---|---|---|
| 0142333 | 5/1985 | European Pat. Off. |
| 0142801 | 5/1985 | European Pat. Off. |
| 2025946 | 1/1980 | United Kingdom |

*Primary Examiner*—Bernard Dentz
*Attorney, Agent, or Firm*—J. Timothy Keane

[57] ABSTRACT

A class of N,N'-cycloalkyl/alkyl benzamides of certain 4H-imidazo[4,5-b]pyridine compounds is described for treating cardiovascular and immuno-inflammatory related disorders mediated by platelet activating factor (PAF). Compounds of particular interest are those of the formula:

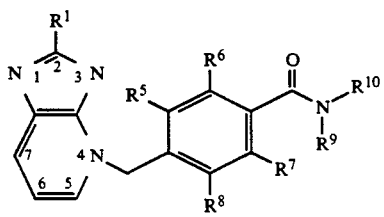

wherein $R^1$ is selected from hydrido, alkyl, hydroxyalkyl, alkoxyalkyl, phenyl, halophenyl, pyridinyl, alkylsilyloxyalkyl, amino, monoalkylamino, dialkylamino, aminoalkyl, monoalkylaminoalkyl and dialkylaminoalkyl; wherein each of $R^5$, $R^6$, $R^7$ and $R^8$ is independently selected from hydrido, hydroxy, alkyl, alkoxy, fluoro, chloro, bromo, haloalkyl, alkylthio, alkoxyalkyl, hydroxyalkyl, alkylthioalkyl, cyano, amino, monoalkylamino and dialkylamino; wherein each of $R^9$ and $R^{10}$ is independently selected from hydrido, alkyl, cycloalkyl, bicycloalkyl, heterocyclic, heterocyclicalkyl, aryl, alkenyl and cycloalkenyl, and wherein any of said $R^9$ and $R^{10}$ substituents may be further substituted with one or more groups selected from linear or branched lower alkyl, lower alkoxy, fluoro, chloro and bromo; or a pharmaceutically-acceptable salt thereof.

20 Claims, No Drawings

N,N'-CYCLOALKYL/ALKYL CARBOXAMIDE 4H-IMIDAZO-[4,5-B]PYRIDINE COMPOUNDS AS PAF ANTAGONISTS

FIELD OF THE INVENTION

This invention is in the field of therapeutics and relates to compounds for treatment of inflammatory and respiratory disorders, such as asthma, vascular disorders, such as cardiovascular and cerebrovascular diseases, and related diseases. Of particular interest is a class of novel N,N'-cycloalkyl/alkyl benzamides of certain 4H-imidazo[4,5-b]pyridine derivatives wherein the phenyl ring of the benzamide group may be substituted with one or more moieties, and which class is useful for treatment of cardiovascular and immuno-inflammatory related disorders mediated by platelet activating factor (PAF).

BACKGROUND OF THE INVENTION

Platelet-activating factor (PAF) has been associated with various biological activities and pathways, thus making it an important mediator responsible for a variety of physiological processes, including activation of platelets, smooth muscle contraction, pathogenesis of immune complex deposition, inflammation, and respiratory, cardiovascular and intravascular alterations. These physiological processes are associated with a large group of diseases, such as cardiovascular disorders, asthma, lung edema, endotoxin shock, adult respiratory distress syndrome and inflammatory diseases.

Various classes of compounds are known for inhibiting platelet activation induced by agents such as arachidonic acid, collagen and platelet activating factor. For example, several classes of imidazole derivatives are known for use in treatment of various cardiovascular and immuno-response diseases related to platelet dysfunction or platelet hyperactivity. U.S. Pat. No. 4,284,641 and No. 4,416,895 to Thorogood describe certain cycloalkyl/cycloalkenyl imidazoles which inhibit platelet aggregation or reduce the adhesive character of platelets by selective inhibition of thromboxane A2. Also described for the same purpose in U.S. Pat. No. 4,357,340 to Thorogood is a class of 1-arylalkylimidazoles. In U.S. Pat. No. 4,243,671 to Harris et al, the compound 1-(3-phenyl-2-propenyl)1H-imidazole is described as effective in inhibiting thromboxane synthetase, arachidonic acid-induced platelet aggregation and bronchoconstriction.

Compounds are known for use in treating platelet dysfunction or platelet hyperactivity induced specifically by platelet activating factor (PAF). For example, a certain class of glycerol derivatives useful as PAF antagonists is described in EP No. 142,333. A class of indene derivatives is described in EP No. 142,801 as PAF inhibitors. Compounds containing heterocyclic moieties of various types are also known as PAF antagonists. For example, U.S. Pat. No. 4,579,862 to Manley et al describes certain imidazole/pyridinylalkanoic acid derivatives as PAF antagonists. U.S. Pat. No. 4,804,658 to Manley et al describes a class of imidazopyridine derivatives useful as PAF inhibitors and mentions, in particular, the compound N-cyclohexyl-N-methyl-4-(1H-imidazo[4,5-c]pyridin-1-yl-methyl)benzamide as an inhibitor of PAF-induced aggregation in an assay using human platelet-rich plasma. U.S. Pat. No. 4,914,108 to Khanna et al describes a class of 5-substituted(4,5-c)imidazopyridine compounds having PAF antagonist activity, including, in particular, the compound 5-[4{-(N-isopropyl,N-cyclohexyl)carboxamido}-2-methoxybenzyl]imidazo[4,5-c]pyridine.

DESCRIPTION OF THE INVENTION

Treatment of platelet-activating-factor-related pathologies, such as PAF-stimulated pathologies or platelet-mediated airway hyper-reactivity, is accomplished by administering to a susceptible subject a therapeutically-effective amount of a compound of a class of compounds represented by Formula I:

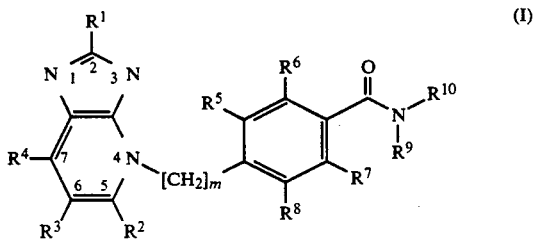

wherein m is a number selected from one through Six, inclusive;

wherein $R^1$ is selected from hydrido, alkyl, hydroxyalkyl, formyl, halo, haloalkyl, cycloalkyl, alkylcycloalkyl, cycloalkylalkyl, cycloalkylhaloalkyl, cycloalkylcarbonyl, alkoxy, aralkyl, aralkylhaloalkyl, aryl, haloaryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, alkylsilyloxyalkyl, aryl/alkylsilyloxyalkyl, arylsilyloxyalkyl, mercaptoalkyl, alkoxycarbonyloxy, alkylthio, alkylthioalkyl, alkylsulfinylalkyl, alkylsulfonylalkyl, cycloalkylthio, cycloalkylalkylthio, alkylcarbonylthio, arylthio, arylcarbonylthio, aralkylthio, aralkylcarbonylthio, and heterocyclic and heterocyclicalkyl having one or more ring atoms selected from oxygen, sulfur and nitrogen atoms;

wherein each of $R^2$, $R^3$ and $R^4$ is independently selected from hydrido, alkyl, hydroxyalkyl, formyl, halo, haloalkyl, cycloalkyl, alkylcycloalkyl, cycloalkylalkyl, cycloalkylhaloalkyl, cycloalkylcarbonyl, alkoxy, aralkyl, aralkylhaloalkyl, alkoxyalkyl, alkylcarbonyl, alkylcarbonylalkyl, alkylsilyloxyalkyl, alkoxycarbonyl, cyano, nitro, alkylthio, alkylthioalkyl, alkylsulfinylalkyl, alkylsulfonylalkyl, cycloalkylthio and cycloalkylalkylthio;

wherein each of $R^5$, $R^6$, $R^7$ and $R^8$ is independently selected from hydrido, alkyl, hydroxy, hydroxyalkyl, formyl, halo, haloalkyl, cycloalkyl, alkylcycloalkyl, cycloalkylalkyl, cycloalkylhaloalkyl, cycloalkylcarbonyl, alkoxy, aralkyl, aralkylhaloalkyl, aryl, haloaryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, alkylsilyoxyalkyl, alkoxycarbonyloxy, alkylthio, alkylthioalkyl, alkylsulfinylalkyl, alkylsulfonylalkyl, cycloalkylthio, cycloalkylalkylthio, alkylcarbonylthio, arylthio, arylcarbonylthio, aralkylthio and aralkylcarbonylthio;

wherein each of $R^1$, $R^2$, $R^3$, $R^4$, $R^5$, $R^6$, $R^7$ and $R^8$ may be further independently selected from amino and amido radicals of the formulae

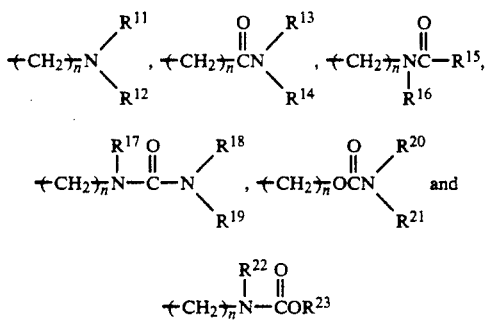

wherein each n is a number independently selected from zero to six, inclusive; wherein each of $R^{11}$ through $R^{23}$ is independently selected from hydrido, alkyl, cycloalkyl, hydroxyalkyl, cycloalkylalkyl, alkoxyalkyl, aralkyl and aryl;

wherein each of $R^9$ and $R^{10}$ is independently selected from hydrido, alkyl, haloalkyl, cycloalkyl, polycycloalkyl, polycycloalkylalkyl, cycloalkylalkyl, aralkyl, aryl, alkenyl, cycloalkenyl, and heterocyclic and heterocyclicalkyl having one or more ring atoms selected from oxygen, sulfur and nitrogen atoms; wherein any of said $R^9$ and $R^{10}$ groups may be substituted at one or more substitutable positions by one or more groups selected from alkyl, halo, haloalkyl and alkoxy; or a pharmaceutically-acceptable salt thereof.

A preferred family of compounds consists of those compounds of Formula I wherein m is a number selected from one through five, inclusive; wherein $R^1$ is selected from hydrido, alkyl, hydroxyalkyl, formyl, halo, haloalkyl, cycloalkyl, alkylcycloalkyl, alkylcycloalkyl, cycloalkylalkyl, cycloalkylhaloalkyl, cycloalkylcarbonyl, alkoxy, aralkyl, aralkylhaloalkyl, aryl, haloaryl, aroyl, aryloxy, aryloxyalkyl, aralkoxy, alkoxyalkyl, alkylcarbonyl, alkylcarbonylalkyl, alkoxycarbonyl, cyano, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, alkylsilyloxyalkyl, aryl/alkylsilyloxyalkyl, arylsilyloxyalkyl, alkylmercaptoalkyl, alkoxycarbonyloxy, alkylthio, alkylthioalkyl, alkylsulfinylalkyl, alkylsulfonylalkyl, arylthio, and heterocyclic and heterocyclicalkyl having one or more ring atoms selected from oxygen, sulfur and nitrogen atoms;

wherein each of $R^2$, $R^3$ and $R^4$ is independently selected from hydrido, alkyl, hydroxyalkyl, formyl, halo, haloalkyl, cycloalkyl, alkylcycloalkyl, cycloalkylalkyl, cycloalkylhaloalkyl, cycloalkylcarbonyl, alkoxy, aralkyl, aralkylhaloalkyl, alkoxyalkyl, alkylcarbonyl, alkylcarbonylalkyl, alkylsilyloxyalkyl, alkoxycarbonyl, cyano, nitro, alkylthio, alkylthioalkyl, alkylsulfinylalkyl and alkylsulfonylalkyl;

wherein each of $R^5$, $R^6$, $R^7$ and $R^8$ is independently selected from hydrido, alkyl, hydroxy, hydroxyalkyl, formyl, halo, haloalkyl, cycloalkyl, alkylcycloalkyl, cycloalkylalkyl, cycloalkylhaloalkyl, cycloalkylcarbonyl, alkoxy, aralkyl, aralkylhaloalkyl, aryl, haloaryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, alkylsilyloxyalkyl, alkoxycarbonyloxy, alkylthio, alkylthioalkyl, alkylsulfinylalkyl, alkylsulfonylalkyl and arylthio;

wherein each of $R^1$, $R^2$, $R^3$, $R^4$, $R^5$, $R^6$, $R^7$ and $R^8$ may be further independently selected from amino and amido radicals of the formulae

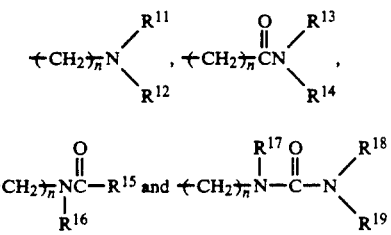

wherein each n is a number independently selected from zero to five, inclusive; wherein each of $R^{11}$ through $R^{19}$ is independently selected from hydrido, alkyl, cycloalkyl, hydroxyalkyl, cycloalkylalkyl, alkoxyalkyl, aralkyl and aryl;

wherein each of $R^9$ and $R^{10}$ is independently selected from hydrido, alkyl, haloalkyl, cycloalkyl, polycycloalkyl, polycycloalkylalkyl, cycloalkylalkyl, aralkyl, aryl, alkenyl, cycloalkenyl, and heterocyclic and heterocyclicalkyl having one or more ring atoms selected from oxygen, sulfur and nitrogen atoms, wherein any of said $R^9$ and $R^{10}$ groups may be substituted at one or more substitutable positions by one or more groups selected from alkyl, halo, haloalkyl and alkoxy; or a pharmaceutically-acceptable salt thereof.

A more preferred family of compounds consists of those compounds of Formula I wherein m is a number selected from one through four, inclusive; wherein $R^1$ is selected from hydrido, alkyl, hydroxyalkyl, halo, haloalkyl, cycloalkyl, alkylcycloalkyl, cycloalkylalkyl, cycloalkylhaloalkyl, alkoxy, aralkyl, aralkylhaloalkyl, aryl, haloaryl, aryloxy, aryloxyalkyl, alkoxyalkyl, alkylcarbonylalkyl, cyano, carboxyalkyl, alkylcarbonyloxyalkyl, alkoxycarbonylalkyl, aralkoxycarbonylalkyl, aralkylcarbonyloxyalkyl, alkylsilyloxyalkyl, aryl/alkylsilyloxyalkyl, arylsilyloxyalkyl, mercaptoalkyl, alkylthio, alkylthioalkyl, alkylsulfinylalkyl, alkylsulfonylalkyl, arylthio, and heterocyclic and heterocyclicalkyl having one or more ring atoms selected from oxygen, sulfur and nitrogen atoms;

wherein each of $R^2$, $R^3$ and $R^4$ is independently selected from hydrido, alkyl, hydroxyalkyl, halo, haloalkyl, cycloalkyl, alkylcycloalkyl, cycloalkylalkyl, cycloalkylhaloalkyl, alkoxy, aralkyl, aralkylhaloalkyl, alkoxyalkyl, alkylcarbonylalkyl, alkylsilyloxyalkyl, cyano, nitro, alkylthio, alkylthioalkyl, alkylsulfinylalkyl and alkylsulfonylalkyl;

wherein each of $R^5$, $R^6$, $R^7$ and $R^8$ is independently selected from hydrido, alkyl, hydroxy, hydroxyalkyl, halo, haloalkyl, cycloalkyl, alkylcycloalkyl, cycloalkylalkyl, alkoxy, aralkyl, aryl, haloaryl, aryloxy, aryloxyalkyl, aralkoxy, alkoxyalkyl, cyano, nitro, carboxyl, carboxyalkyl, alkylcarbonyloxy, alkylsilyloxyalkyl, alkoxycarbonyloxy, alkylthio, alkylthioalkyl, alkylsulfinylalkyl, alkylsulfonylalkyl and arylthio;

wherein each of $R^1$, $R^2$, $R^3$, $R^4$, $R^5$, $R^6$, $R^7$ and $R^8$ may be further independently selected from amino and amido radicals of the formulae

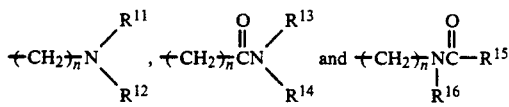

wherein each n is a number independently selected from zero to four, inclusive; wherein each of $R^{11}$ through $R^{16}$ is independently selected from hydrido, alkyl, cycloalkyl, hydroxyalkyl, cycloalkylalkyl, alkoxyalkyl, aralkyl and aryl;

wherein each of $R^9$ and $R^{10}$ is independently selected from hydrido, alkyl, haloalkyl, cycloalkyl, polycycloalkyl, polycycloalkylalkyl, cycloalkylalkyl, aralkyl, aryl, alkenyl, cycloalkenyl, and heterocyclic and heterocyclicalkyl having one or more ring atoms selected from oxygen, sulfur and nitrogen atoms, wherein any of said $R^9$ and $R^{10}$ groups may be substituted at one or more substitutable positions by one or more groups selected from alkyl, halo, haloalkyl and alkoxy, with the proviso that when $R^9$ or $R^{10}$ is an alkenyl or a cycloalkenyl group, then the double bond of such group cannot be adjacent to the nitrogen atom of the amido group of Formula I; or a pharmaceutically-acceptable salt thereof.

An even more preferred family of compounds consists of those compounds of Formula I wherein m is a number selected from one through three, inclusive;

wherein $R^1$ is selected from hydrido, alkyl, hydroxyalkyl, halo, haloalkyl, cycloalkyl, alkylcycloalkyl, cycloalkylalkyl, cycloalkylhaloalkyl, alkoxy, phenylalkyl, phenyl, halophenyl, phenoxy, phenoxyalkyl, alkoxyalkyl, cyano, alkylsilyloxyalkyl, phenyl/alkylsilyloxyalkyl, phenylsilyloxyalkyl, alkylthio, phenylthio, and heterocyclic and heterocyclicalkyl having one or more ring atoms selected from oxygen, sulfur and nitrogen atoms;

wherein each of $R^2$, $R^3$ and $R^4$ is independently selected from hydrido, alkyl, hydroxyalkyl, halo, haloalkyl, cycloalkyl, alkylcycloalkyl, cycloalkylalkyl, alkoxy, phenylalkyl, alkoxyalkyl, alkylcarbonylalkyl, alkylsilyloxyalkyl, cyano, nitro and alkylthio;

wherein each of $R^5$, $R^6$, $R^7$ and $R^8$ is independently selected from hydrido, alkyl, hydroxy, hydroxyalkyl, halo, haloalkyl, cycloalkyl, alkylcycloalkyl, cycloalkylalkyl, alkoxy, phenylalkyl, phenyl, halophenyl, phenyloxy, phenyloxyalkyl, alkoxyalkyl, cyano, nitro, carboxyalkyl, alkylsilyloxyalkyl, alkylthio and phenylthio;

wherein each of $R^1$, $R^2$, $R^3$, $R^4$, $R^5$, $R^6$, $R^7$ and $R^8$ may be further independently selected from amino and amido radicals of the formulae

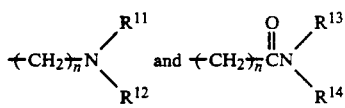

wherein each n is a number independently selected from zero to four, inclusive; wherein each of $R^{11}$ through $R^{14}$ is independently selected from hydrido, alkyl, cycloalkyl, hydroxyalkyl, cycloalkylalkyl, alkoxyalkyl, phenylalkyl and phenyl;

wherein each of $R^9$ and $R^{10}$ is independently selected from hydrido, alkyl, haloalkyl, cycloalkyl, bicycloalkyl, bicycloalkylalkyl, cycloalkylalkyl, phenylalkyl, phenyl, o alkenyl, cycloalkenyl, heterocyclic and heterocyclicalkyl having one or more ring atoms selected from oxygen, sulfur and nitrogen atoms, wherein any of said $R^9$ and $R^{10}$ groups may be substituted at one or more substitutable positions by one or more groups selected from alkyl, halo, haloalkyl and alkoxy, with the proviso that when $R^9$ or $R^{10}$ is an alkenyl or a cycloalkenyl group, then the double bond of such group cannot be adjacent to the nitrogen atom of the amido group of Formula I; or a pharmaceutically-acceptable salt thereof.

A highly preferred family of compound consists of compounds of Formula I wherein m is one or two; wherein $R^1$ is selected from hydrido, alkyl, hydroxyalkyl, halo, haloalkyl, cycloalkyl, alkylcycloalkyl, cycloalkylalkyl, cycloalkylhaloalkyl, alkoxy, benzyl, phenyl, halophenyl, alkoxyalkyl, alkylsilyloxyalkyl, phenyl/alkylsilyloxyalkyl, phenylsilyloxyalkyl, alkylthio, furanyl and pyridinyl;

wherein each of $R^2$, $R^3$ and $R^4$ is independently selected from hydrido, alkyl, hydroxyalkyl, halo, haloalkyl, cycloalkyl, alkylcycloalkyl, cycloalkylalkyl, alkoxy, benzyl, alkoxyalkyl, alkylsilyloxyalkyl and alkylthio;

wherein each of $R^5$, $R^6$, $R^7$ and $R^8$ is independently selected from hydrido, alkyl, hydroxy, hydroxyalkyl, formyl, halo, haloalkyl, cycloalkyl, alkylcycloalkyl, cycloalkylalkyl, alkoxy, alkoxyalkyl, alkylsilyloxyalkyl and alkylthio;

wherein each of $R^1$, $R^2$, $R^3$, $R^4$, $R^5$, $R^6$, $R^7$ and $R^8$ may be further independently selected from amino radicals of the formula

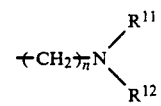

wherein each n is a number independently selected from zero to four, inclusive; wherein each of $R^{11}$ and $R^{12}$ is independently selected from hydrido, alkyl, cycloalkyl, hydroxyalkyl, cycloalkylalkyl, alkoxyalkyl, benzyl and phenyl;

wherein each of $R^9$ and $R^{10}$ is independently selected from hydrido, alkyl, haloalkyl, cycloalkyl, bicycloalkyl, bicycloalkylalkyl, cycloalkylalkyl, phenylalkyl, phenyl, saturated or partially saturated heterocyclicalkyl having 4 to 8 ring atoms, heteroaryl having 5 or 6 ring atoms, alkenyl and cycloalkenyl; wherein any of said $R^9$ and $R^{10}$ groups may be substituted at one or more substitutable positions by one or more groups selected from alkyl, halo, haloalkyl and alkoxy, with the proviso that when $R^9$ or $R^{10}$ is an alkenyl or a cycloalkenyl group, then the double bond of such group cannot be adjacent to the nitrogen atom of the amido group of Formula I; or a pharmaceutically-acceptable salt thereof.

A more highly preferred family of compounds consists of those compounds of Formula I wherein m is one; wherein $R^1$ is selected from hydrido, alkyl, hydroxyalkyl, alkoxyalkyl, phenyl, halophenyl, furanyl, pyridinyl, alkylsilyloxyalkyl, amino, monoalkylamino, dialkylamino, aminoalkyl, mcnoalkylaminoalkyl and dialkylaminoalkyl, wherein when $R^1$ is alkyl or is a group containing alkyl, then such alkyl has one to about six carbon atoms and may have a linear or branched configuration;

wherein each of $R^2$, $R^3$ and $R^4$ is hydrido;

wherein each of $R^5$, $R^6$, $R^7$ and $R^8$ is independently selected from hydrido, hydroxy, alkyl, alkoxy, fluoro, chloro, bromo, haloalkyl, alkylthio, alkoxyalkyl, hydroxyalkyl, alkylthioalkyl, cyano, amino, monoalkylamino, dialkylamino, aminoalkyl, monoalkylaminoalkyl and dialkylaminoalkyl; wherein when any of the foregoing $R^5$, $R^6$, $R^7$ and $R^8$ is alkyl or is a group containing alkyl, such alkyl has one to about six carbon atoms and may have a linear or branched configuration;

wherein each of $R^9$ and $R^{10}$ is independently selected from hydrido, linear or branched chain alkyl having 1 to about 15 carbon atoms, cycloalkyl having 3 to about 8 carbon atoms, bicycloalkyl having 3 to about 8 carbon atoms in each ring, saturated or partially saturated heterocyclicalkyl having 4 to 8 ring atoms, heteroaryl having 5 or 6 ring atoms, phenyl, linear or branched alkenyl having 3 to about 15 carbon atoms with the proviso that the double bond of the alkenyl group cannot be adjacent to the nitrogen, cycloalkenyl having 5 to about 8 carbon atoms with the proviso that the double bond cannot be adjacent to the nitrogen of the amido group of Formula I, and wherein any of said $R^9$ and $R^{10}$ substituents may be further substituted with one or more groups selected from linear or branched lower alkyl, lower alkoxy, chloro and bromo; or a pharmaceutically-acceptable salt thereof.

An even more highly preferred family of compounds consists of those compounds of Formula I wherein m is one; wherein $R^1$ is selected from hydrido, methyl, ethyl, n-propyl, isopropyl, n-butyl, isobutyl, sec-butyl, tert-butyl, n-pentyl, isopentyl, neopentyl, hexyl, hydroxymethyl, hydroxyethyl, hydroxypropyl, hydroxybutyl, methoxymethyl, ethoxymethyl, propoxymethyl, butoxymethyl, methoxyethyl, methoxypropyl, methoxybutyl, ethoxyethyl, ethoxypropyl, ethoxybutyl, propoxymethyl, propoxyethyl, propoxypropyl, propoxybutyl, butoxymethyl, butoxyethyl, butoxypropyl, butoxybutyl, phenyl, monofluorophenyl, difluorophenyl, monochlorophenyl, dichlorophenyl, monobromophenyl, dibromophenyl, trimethylsilyloxymethyl, trimethylsilyloxyethyl, trimethylsilyloxypropyl, trimethylsilyloxybutyl, triethylsilyloxymethyl, triethylsilyloxyethyl, triethylsilyloxypropyl, triethylsilyloxybutyl, tripropylsilyloxymethyl, tripropylsilyloxyethyl, tripropylsilyloxypropyl, tripropylsilyloxybutyl, tert-butyl(dimethyl)silyloxymethyl, tert-butyl(dimethyl)silyloxyethyl, tert-butyl(dimethyl)silyloxypropyl, tert-butyl(dimethyl)silyloxybutyl, 2-pyridinyl, 3-pyridinyl, amino, N-methylamino, N,N'-dimethylamino, N-ethylamino, N,N'-diethylamino, N-propylamino, N,N'-dipropylamino, N-butylamino, N-N'-dibutylamino, N-methylaminomethyl, N-methylaminoethyl, N-methylaminopropyl, N-methylaminobutyl, N,N'-dimethylaminomethyl, N,N'-dimethylaminoethyl, N,N'-dimethylaminopropyl, N,N'-dimethylaminobutyl, N,N'-diethylaminomethyl, N,N'-diethylaminoethyl, N,N'-diethylaminopropyl, N,N'-diethylaminobutyl, N,N'-dipropylaminomethyl, N,N'-dipropylaminoethyl, N,N'-dipropylaminopropyl, N,N'-dipropylaminobutyl, N,N'-dibutylaminomethyl, N,N'-dibutylaminoethyl, N,N'-dibutylaminopropyl and N,N'-dibutylaminobutyl, wherein when $R^1$ is alkyl group or is one of the foregoing groups containing an alkyl group, such alkyl group may be linear or branched in configuration;

wherein each of $R^2$, $R^3$ and $R^4$ is hydrido;

wherein each of $R^5$, $R^6$, $R^7$ and $R^8$ is independently selected from hydrido, methyl, ethyl, n-propyl, isopropyl, n-butyl, isobutyl, sec-butyl, tert-butyl, n-pentyl, isopentyl, neopentyl, hexyl, fluoro, chloro, bromo, hydroxy, methoxy, ethoxy, propoxy, butoxy, pentoxy, trifluoromethyl, perfluoroethyl, dichloromethyl, methylthio, ethylthio, propylthio, butylthio, pentylthio, hydroxymethyl, hydroxyethyl, hydroxypropyl, hydroxybutyl, methoxymethyl, ethoxymethyl, propoxymethyl, butoxymethyl, methoxyethyl, methoxypropyl, methoxybutyl, ethoxyethyl, ethoxypropyl, ethoxybutyl, propoxymethyl, propoxyethyl, propoxypropyl, propoxybutyl, butoxymethyl, butoxyethyl, butoxypropyl, butoxybutyl, methylthiomethyl, methylthioethyl, methylthiopropyl, methylthiobutyl, ethylthiomethyl, ethylthioethyl, ethylthiopropyl, ethylthiobutyl, propylthiomethyl, propylthioethyl, propylthiopropyl, propylthiobutyl, butylthiomethyl, butylthioethyl, butylthiopropyl, butylthiobutyl, cyano, amino, N-methylamino, N,N'-dimethylamino, N-ethylamino, N,N'-diethylamino, N-propylamino, N,N'-dipropylamino, N-butylamino, N-N'-dibutylamino, N-methylaminomethyl, N-methylaminoethyl, N-methylaminopropyl, N-methylaminobutyl, N,N'-dimethylaminomethyl, N,N'-dimethylaminoethyl, N,N'-dimethylaminopropyl, N,N'-dimethylaminobutyl, N,N'-diethylaminomethyl, N,N'-diethylaminoethyl, N,N'-diethylaminopropyl, N,N'-diethylaminobutyl, N,N'-dipropylaminomethyl, N,N'-dipropylaminoethyl, N,N'-dipropylaminopropyl, N,N'-dipropylaminobutyl, N,N'-dibutylaminomethyl, N,N'-dibutylaminoethyl, N,N'-dibutylaminopropyl and D N,N -dibutylaminobutyl; wherein when any of $R^5$, $R^6$, $R^7$ and $R^8$ is alkyl or is a group containing alkyl, such alkyl group may be linear or branched in configuration;

wherein each of $R^9$ and $R^{10}$ is independently selected from hydrido, methyl, ethyl, n-propyl, isopropyl, isobutyl, sec-butyl, tert-butyl, n-pentyl, isopentyl, neopentyl, n-hexyl, n-heptyl, n-octyl, n-nonyl, n-decyl, 1,1,3,3-tetramethylbutyl, 2,2-dimethylethyl, 1,1-diethylmethyl, cyclopropyl, cyclobutyl, cyclohexyl, cycloheptyl, cyclooctyl, methylcyclopentyl, ethylcyclopentyl, 2-methylcyclohexyl, 3-methylcyclohexyl, 4-methylcyclohexyl, 3,5-dimethylcyclohexyl, ethylcyclohexyl, 3,5-diethylcyclohexyl, decalin, norbornyl, 2,2,1-bicycloheptyl, 2,2,1-bicycloheptylmethyl, phenyl, furanyl, pyranyl, oxetanyl, pyrrolidinyl, piperidinyl, tetrahydrothiophenyl, thiopyranyl, morpholino, piperazinyl, furanylmethyl, pyranylmethyl, oxetanylmethyl, pyrrolidinylmethyl, piperidinylmethyl, tetrahydrothiophenylmethyl, thiopyranylmethyl, morpholinomethyl, piperazinylmethyl, pyrrole, pyrrolemethyl, pyrazole, pyrazolemethyl, imidazole, imidazolemethyl, triazole, triazolemethyl, tetrazole, tetrazolemethyl, pyrazinyl, pyrazinylmethyl, thiazole, thiazolemethyl, oxazole, oxazolemethyl, 2-pyridinyl, 3-pyridinyl, 2-pyridinylmethyl and 3-pyridinylmethyl; or a pharmaceutically-acceptable salt thereof.

The term "hydrido" denotes a single hydrogen atom (H). This hydrido group may be attached, for example, to an oxygen atom to form a hydroxyl group; or, as another example, one hydrido group may be attached to a carbon atom to form a >CH— group; or, as another example, two hydrido groups may be attached to a carbon atom to form a —CH$_2$— group. Where the term "alkyl" is used, either alone or within other terms such as "haloalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. The term "cycloalkyl" embraces mono-carbocyclic saturated radicals having three to about ten ring carbon atoms, preferably three to about six carbon atoms, such as cyclopropyl, cyclobutyl, cyclopentyl and cyclohexyl. The term "cycloalkylalkyl" denotes a cycloalkyl radical attached to an alkyl radical which is attachable to a substitutable position of Formula I. Examples of "cycloalkylalkyl" radicals are cyclopentylmethyl and cyclohexylethyl. The term "polycycloalkyl" denotes a ring system radical formed by two, or by three, or by more, cycloalkyl radicals joined together through one common carbon atom, or through two common adjacent carbon atoms to form a two-ring fused ring system, or formed by an alkylene bridge across a cycloalkyl ring. Such polycycloalkyl ring systems may contain from four to about twenty carbon atoms, and more preferably from eight to about ten carbon atoms. An example of a "polycycloalkyl" radical is adamantyl, also known as tricyclodecyl radical. The term "polycycloalkylalkyl" denotes a polycycloalkyl radical attached to an alkyl radical which is attachable to a substitutable position of Formula I. Examples of "polycycloalkylalkyl" radicals are adamantylmethyl and adamantylethyl. Included within the term "polycycloalkyl" is the term "bicycloalkyl" which denotes a fused ring system having two fused cycloalkyl rings collectively composed of seven to about twelve carbon atoms. The term "haloalkyl" embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group, such as monofluoromethyl. Dihaloalkyl and polyhaloalkyl groups may be substituted with two or more of the same halo groups, or may have a combination of different halo groups. A dihaloalkyl group, for example, may have two fluoro atoms, such as difluoromethyl and difluorobutyl groups, or two chloro atoms, such as a dichloromethyl group, or one fluoro atom and one chloro atom, such as a fluorochloromethyl group. Examples of a polyhaloalkyl are trifluoromethyl, 1,1-difluoroethyl, 2,2,2-trifluoroethyl, perfluoroethyl, 2,2,3,3-tetrafluoropropyl and perfluoropropyl groups. The term "difluoroalkyl" embraces alkyl groups having two fluoro atoms substituted on any one or two of the alkyl group carbon atoms. The terms "alkylol" and "hydroxyalkyl" embrace linear or branched alkyl groups having one to about ten carbon atoms any one of which may be substituted with one or more hydroxyl groups. The term "alkylsilyloxyalkyl" embraces a silyloxyalkylene group wherein such group is attached to the nucleus of Formula I through its alkylene moiety and which group has three terminal alkyl moieties attached to the silyl portion of such group. Similarly, the term "aryl/alkylsilyloxyalkyl" embraces a silyloxyalkylene group wherein such group is attached to the nucleus of Formula I through its alkylene moiety and which group has three terminal moieties selected from alkyl and aryl, which three moieties are attached to the silyl portion of such group. Similarly, the term "arylsilyloxyalkyl" embraces a silyloxyalkylene group wherein such group is attached to the nucleus of Formula I through its alkylene moiety and which group has three terminal aryl moieties attached to the silyl portion of such group. The term "alkenyl" embraces linear or branched radicals having two to about twenty carbon atoms, preferably three to about ten carbon atoms, and containing at least one carbon-carbon double bond, which carbon-carbon double bond may have either cis or trans geometry within the alkenyl moiety, relative to groups substituted on the double-bonded carbons. The term "alkynyl" embraces linear or branched radicals having two to about twenty carbon atoms, preferably two to about ten carbon atoms, and containing at least one carbon-carbon triple bond. The term "cycloalkenyl" embraces cyclic radicals having three to about ten ring carbon atoms including one or more double bonds involving adjacent ring carbons. The terms "alkoxy" and "alkoxyalkyl" embrace linear or branched oxy-containing radicals each having alkyl portions of one to about ten carbon atoms. An example of alkoxy is methoxy group. The term "alkoxyalkyl" also embraces alkyl radicals having two or more alkoxy groups attached to an alkyl radical. The term "dialkoxyalkyl" is exemplified by dimethoxymethyl and 2,2-diethoxyethyl. The "alkoxy" or "alkoxyalkyl" radicals may be further substituted with one or more halo atoms, such as fluoro, chloro or bromo, to provide haloalkoxy or haloalkoxyalkyl groups. The term "alkylthio" embraces radicals containing a linear or branched alkyl group, of one to about ten carbon atoms attached to a divalent sulfur atom, such as a methythio group. The terms "sulfinyl" and "sulfonyl", whether used alone or linked to other terms such as "alkyl", denote —SO— and —SO$_2$—, respectively. The term "aryl" denotes a carbocyclic aromatic ring system composed of one or more aromatic rings. Preferred aryl groups are those consisting of one, two, or three benzene rings. The term "aryl" embraces aromatic radicals such as phenyl, naphthyl and biphenyl. The term "aralkyl" embraces aryl-substituted alkyl radicals such as benzyl, diphenylmethyl, triphenylmethyl, phenylethyl, phenylbutyl and diphenylethyl. The terms "benzyl" and "phenylmethyl" are interchangeable. The terms "aryloxy" and "arylthio" denote, respectively, aryl groups having an oxygen or sulfur atom through which the radical is attached to a nucleus, examples of which are phenoxy and phenylthio. The term "aralkoxy", alone or within another term, embraces an aryl group attached to an alkoxy group to form, for example, benzyloxy. The term "acyl" whether used alone, or within terms such as acyloxy and acylaminoalkyl, denotes a radical provided by the residue after removal of hydroxyl from an organic acid, examples of such radical being acetyl and benzoyl. "Lower alkanoyl" is an example of a more preferred sub-class of acyl. The term "amido" denotes a radical consisting of nitrogen atom attached to a carbonyl group, which radical may be further substituted in the manner described herein. The amido radical can be attached to the nucleus of a compound of the invention through the carbonyl moiety or through the nitrogen atom of the amido radical. The term "alkenylalkyl" denotes a radical having a double-bond unsaturation site between two carbons, and which radical is further substituted with alkyl groups which may optionally contain additional double-bond unsaturation.

The terms "heterocyclic" and "heterocyclicalkyl" embrace ring systems of four to ten ring members with at least one ring member being a hetero atom selected from oxygen, sulfur and nitrogen atom, wherein said ring system may be monocyclic or bicyclic and may be fully saturated or partially saturated or fully unsaturated, and may be fused to a benzene or cyclohexane ring, wherein the point of attachment of the ring system to the backbone of the structure of Formula I may be through a bond to any substitutable position on said heterocyclic ring system or through an alkyl group interposed between the ring system and the point of attachment to Formula I, and wherein any substitutable position of the ring system may be optionally substituted with one or more radicals selected from alkyl, alkoxy, alkenyl, alkynyl, halo, trifluoromethyl, oxo, cyano and phenyl, and wherein the said heterocyclic ring nitrogen atom may be combined with oxygen to form an N-oxide. Within the term "heterocyclic" ring system are the subset terms "heteroaryl" and "heteroarylalkyl". The term "heteroaryl" embraces aromatic ring systems containing one or two hetero atoms selected from oxygen, nitrogen and sulfur in a ring system having five or six ring members, examples of which are thienyl, furanyl, imidazolyl, pyrazolyl, triazolyl, tetrazolyl, pyridinyl, thiazolyl, pyrimidyl and isoxazolyl. Such heteroaryl may be attached as a substituent through a carbon atom of the heteroaryl ring system, or may be attached through a carbon atom of a moiety substituted on a heteroaryl ring-member carbon atom, for example, through the methylene substituent of imidazolemethyl moiety.

For any of the foregoing defined radicals, preferred radicals are those containing from one to about twelve carbon atoms.

Specific examples of alkyl groups are methyl, ethyl, n-propyl, isopropyl, n-butyl, sec-butyl, isobutyl, tert-butyl, n-pentyl, isopentyl, methylbutyl, dimethylbutyl, neopentyl and hexyl. Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated bonds.

Included within the family of compounds of Formula I are the tautomeric forms of the described compounds, as well as the stereoisomers including diastereoisomers and enantiomers, and pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, ethanesulfonic, 2-hydroxyethanesulfonic, pantothenic, benzenesulfonic, toluenesulfonic, sulfanilic, mesylic, cyclohexylaminosulfonic, stearic, algenic, $\beta$-hydroxy, butyric, malonic, galactaric and galacturonic acid. Suitable pharmaceutically-acceptable base addition salts of compounds of Formula I include metallic salts made from aluminium, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

Compounds of Formula I or their physiologically-acceptable or pharmaceutically-acceptable salts have a potential PAF-antagonistic activity and are of potential value therapeutically as active components in pharmaceutical compositions. Platelet activating factor (PAF) is the phospholipid "1-0-alkyl-2-acetyl-sn-glycero-3-phosphocholine" (AGEPC) which is known as a potent lipid mediator released by animal and human proinflammatory cells. These cells include primarily basophilic and neutrophilic granulocytes, endothelial cells, fibroblasts, epithelial brain cells, macrophages (from blood and tissue) and thrombocytes which are involved in inflammatory reactions.

In pharmacological trials, PAF may cause bronchoconstriction, a lowering of blood pressure, the triggering of thrombocyte aggregation and a proinflammatory activity. Thus PAF is indicated, directly or indirectly, as a mediator in anaphylaxis, in the pathophysiology of allergic conditions, bronchial asthma and in inflammations in general. Compounds of Formula I are therefore suitable for treating patients affected by diseases in which PAF is implicated, including inflammatory or allergic processes or autoimmune diseases. Examples of indications for a PAF antagonist include inflammatory processes of the tracheobronchial tree (acute and chronic bronchitis, bronchial asthma) or of the kidneys (glomerulonephritis), the joints (rheumatic complaints), anaphylactic conditions, allergies and inflammation in the mucous membranes (rhinitis, conjunctivitis) and the skin (e.g. psoriasis, atopic eczema, cold-induced urticaria) and shock caused by sepsis, endotoxins, trauma or burns.

Other important indications for a PAF antagonist include the following: lesions and inflammation in the gastric and intestinal linings, such as shock ulcers, ulcerative colitis, Crohn's disease, ischemic bowel necrosis, stress ulcers and peptic ulcers in general, but particularly ventricular and duodenal ulcers; obstructive lung diseases such as bronchial hyper-reactivity; inflammatory diseases of the pulmonary passages, such as chronic bronchitis; cardio/circulatory diseases such as polytrauma, anaphylaxis and arteriosclerosis; inflammatory intestinal diseases, EPH gestosis (edema-proteinuria hypertension); diseases of extracorporeal circulation, e.g. heart insufficiency, cardiac infarct, organ damage caused by high blood pressure, ischaemic diseases, inflammatory and immunological diseases; immune modulation in the transplanting of foreign tissues, e.g. the rejection of kidney, liver an other transplants; immune modulation in leukemia; propagation of metastasis, e.g. in bronchial neoplasia; diseases of the CNS, such as migraine, multiple sclerosis, endogenic depression and agarophobia (panic disorder). Compounds of Formula I could also be effective as follows: as cyto- and organo-protective agents, e.g. for neuroprotection; to treat DIC (disseminated intravascular coagulation); to treat side effects of drug therapy, e.g. anaphylactoid circulatory reactions; to treat incidents caused by contrast media and other side effects in tumor therapy; to diminish incompatibilities in blood transfusions; to prevent fulminant liver failure ($CCl_4$ intoxication); to treat amanita phalloides intoxication (mushroom poisoning); to treat symptoms of parasitic diseases (e.g. worms); to treat autoimmune diseases (e.g. Werlhof s disease); to treat autoimmune hemolytic anemia, autoimmunologically induced glomerulonephritis, thyroids Hashimoto, primary myxoedema, pernicious anemia, autoimmune atrophic gastritis, Addison's disease, juvenile diabetes, Goodpasture syndrome, idiopathic leukopenia, primary biliary cirrhosis, active or chronically aggressive hepatitis (HBsAg-neg.), ulcerative colitis and systemic lupus erythematodes (SLE), idiopathic thrombocytopenic purpura (ITP); to treat diabetes, diabetic retinopathy, polytraumatic shock, haemorrhagic shock; and to treat PAF-associated interaction with tissue hormones (autocoid hormones), lymphokines and other mediators.

Compounds of the invention may also be used in combinations for which PAF-antagonists are suitable, e.g. with $\beta$-adrenergics, parasympatholytics, corticosteroids, antiallergic agents and secretolytics. When compounds of Formula I are combined with TNF (tumor necrosis factor), the TNF is likely to be better tolerated (elimination of disturbing side effects). Thus, TNF may be used in higher dosages than when it is administered alone. The term "combination" here also includes the administration of the two active substances in separate preparations simultaneously or in sequence over a time period. When compounds are administered in combination with $\beta$-adrenergics, a synergistic effect may be achieved.

A family of specific compounds of particular interest within Formula I consists of compounds, and their pharmaceutically-acceptable salts, of the following group:

4-(4H-imidazo[4,5-b]pyridin-4-ylmethyl)-3-methoxybenzoic acid, N-cyclobutyl-N-cyclohexyl amide;
4-(4H-imidazo[4,5-b]pyridin-4-ylmethyl)-3-methoxybenzoic acid, N-cyclopropyl-N-cyclohexyl amide;
4-(4H-imidazo[4,5-b]pyridin-4-ylmethyl)-3-ethoxybenzoic acid, N-cyclopentyl-N-cyclopentyl amide;
4-(4H-imidazo[4,5-b]pyridin-4-ylmethyl)-3-methoxybenzoic acid, N-isopropyl N-cyclopentyl amide;
4-(4H-imidazo[4,5-b]pyridin-4-ylmethyl)-3-methoxybenzoic acid, N-cyclohexyl-N-cyclohexyl amide;
4-(4H-imidazo[4,5-b]pyridin-4-ylmethyl)-3-methoxybenzoic acid, N-2-butyl-N-cyclohexyl amide;
4-(4H-imidazo[4,5-b]pyridin-4-ylmethyl)-3-methoxybenzoic acid, N-phenyl-N-cyclohexyl amide;
4-(4H-imidazo[4,5-b]pyridin-4-ylmethyl)-3-methoxybenzoic acid, N-3-pentyl-N-cyclohexyl amide;
4-(4H-imidazo[4,5-b]pyridin-4-ylmethyl)-3-methoxybenzoic acid, N-3-methylcyclohexyl-N-cyclopentyl amide;
4-(4H-imidazo[4,5-b]pyridin-4-ylmethyl)-3-methoxybenzoic acid, N-4-methylcyclohexyl-N-cyclopentyl amide;
4-(4H-imidazo[4,5-b]pyridin-4-ylmethyl)-3-methoxybenzoic acid, N-2-methylcyclohexyl-N-cyclopentyl amide;
4-(4H-imidazo[4,5-b]pyridin-4-ylmethyl)-3-methoxybenzoic acid, N-2-methylcyclohexyl-N-isopropyl amide;
4-(4H-imidazo[4,5-b]pyridin-4-ylmethyl)-3-methoxybenzoic acid, N-3-methylcyclohexyl-N-isopropyl amide;
4-(4H-imidazo[4,5-b]pyridin-4-ylmethyl)-3-methoxybenzoic acid, N-3,5-dimethylcyclohexyl-N-isopropyl amide;
4-(4H-imidazo[4,5-b]pyridin-4-ylmethyl)-2-methoxybenzoic acid, N-cyclobutyl-N-cyclohexyl amide;
4-(4H-imidazo[4,5-b]pyridin-4-ylmethyl)-2-methoxybenzoic acid, N-cyclopropyl-N-cyclohexyl amide;
4-(4H-imidazo[4,5-b]pyridin-4-ylmethyl)-2-methoxybenzoic acid, N-cyclopentyl-N-cyclopentyl amide;
4-(4H-imidazo[4,5-b]pyridin-4-ylmethyl)-2-methoxybenzoic acid, N-isopropyl-N-cyclopentyl amide;
4-(4H-imidazo[4,5-b]pyridin-4-ylmethyl)-2-methoxybenzoic acid, N-cyclohexyl-N-cyclohexyl amide;
4-(4H-imidazo[4,5-b]pyridin-4-ylmethyl)-2-methoxybenzoic acid, N-2-butyl-N-cyclohexyl amide;
4-(4H-imidazo[4,5-b]pyridin-4-ylmethyl)-2-methoxybenzoic acid, N-phenyl-N-cyclohexyl amide;
4-(4H-imidazo[4,5-b]pyridin-4-ylmethyl)-2-methoxybenzoic acid, N-3-pentyl-N-cyclohexyl amide;
4-(4H-imidazo[4,5-b]pyridin-4-ylmethyl)-2-methoxybenzoic acid, N-3-methylcyclohexyl-N-cyclopentyl amide;
4-(4H-imidazo[4,5-b]pyridin-4-ylmethyl)-2-methoxybenzoic acid, N-4-methylcyclohexyl-N-cyclopentyl amide;
4-(4H-imidazo[4,5-b]pyridin-4-ylmethyl)-2-methoxybenzoic acid, N-2-methylcyclohexyl-N-cyclopentyl amide;
4-(4H-imidazo[4,5-b]pyridin-4-ylmethyl)-2-methoxybenzoic acid, N-2-methylcyclohexyl-N-isopropyl amide;
4-(4H-imidazo[4,5-b]pyridin-4-ylmethyl)-2-methoxybenzoic acid, N-3-methylcyclohexyl-N-isopropyl amide;
4-(4H-imidazo[4,5-b]pyridin-4-ylmethyl)-2-methoxybenzoic acid, N-3,5-dimethylcyclohexyl-N-isopropyl amide;
4-[(2-methyl-4H-imidazo[4,5-b]pyridin-4-yl)methyl]-3-methoxybenzoic acid, N-cyclobutyl-N-cyclohexyl amide;
4-[(2-methyl-4H-imidazo[4,5-b]pyridin-4-yl)methyl]-3-methoxybenzoic acid, N-cyclopropyl-N-cyclohexyl amide;
4-[(2-methyl-4H-imidazo[4,5-b]pyridin-4-yl)methyl]-3-methoxybenzoic acid, N-cyclopentyl-N-cyclopentyl amide;
4-[(2-methyl-4H-imidazo[4,5-b]pyridin-4-yl)methyl]-3-methoxybenzoic acid, N-isopropyl-N-cyclopentyl amide;
4-[(2-methyl-4H-imidazo[4,5-b]pyridin-4-yl)methyl]-3-methoxybenzoic acid, N-cyclohexyl-N-cyclohexyl amide;
4-[(2 methyl-4H-imidazo[4,5-b]pyridin-4-yl)methyl]-3-methoxybenzoic acid, N-2-butyl-N-cyclohexyl amide;
4-[(2-methyl-4H-imidazo[4,5-b]pyridin-4-yl)methyl]-3-methoxybenzoic acid, N-phenyl-N-cyclohexyl amide;
4-[(2-methyl-4H-imidazo[4,5-b]pyridin-4-yl)methyl]-3-methoxybenzoic acid, N-3-pentyl-N-cyclohexyl amide;
4-[(2-methyl-4H-imidazo[4,5-b]pyridin-4-yl)methyl]-3-methoxybenzoic acid, N-3-methylcyclohexyl-N-cyclopentyl amide;
4-[(2-methyl-4H-imidazo[4,5-b]pyridin-4-yl)methyl]-3-methoxybenzoic acid, N-4-methylcyclohexyl-N-cyclopentyl amide;
4-[(2-methyl-4H-imidazo[4,5-b]pyridin-4-yl)methyl]-3-methoxybenzoic acid, N-2-methylcyclohexyl-N-cyclopentyl amide;
4-[(2-methyl-4H-imidazo[4,5-b]pyridin-4-yl)methyl]-3-methoxybenzoic acid, N-2-methylcyclohexyl-N-isopropyl amide;
4-[(2-methyl-4H-imidazo[4,5-b]pyridin-4-yl)methyl]-3-methoxybenzoic acid, N-3-methylcyclohexyl-N-isopropyl amide;

4-[(2-methyl-4H-imidazo[4,5-b]pyridin-4-yl)methyl]-3-methoxybenzoic acid, N-3,5-dimethylcyclohexyl-N-isopropyl amide;

4-[(2-(hydroxymethyl)-4H-imidazo[4,5-b]pyridin-4-yl)methyl]-3-methoxybenzoic acid, N-cyclobutyl-N-cyclohexyl amide;

4-[(2-(hydroxymethyl)-4H-imidazo[4,5-b]pyridin-4-yl)methyl]-3-methoxybenzoic acid, N-cyclopropyl-N-cyclohexyl amide;

4-[(2-(hydroxymethyl)-4H-imidazo[4,5-b]pyridin-4-yl)methyl]-3-methoxybenzoic acid, N-cyclopentyl-N-cyclopentyl amide;

4-[(2-(hydroxymethyl)-4H-imidazo[4,5 b]pyridin-4-yl)methyl]-3-methoxybenzoic acid, N-isopropyl-N-cyclopentyl amide;

4-[(2-(hydroxymethyl)-4H-imidazo[4,5-b]pyridin-4-yl)methyl]-3-methoxybenzoic acid, N-cyclohexyl-N-cyclohexyl amide;

4-[(2-(hydroxymethyl)-4H-imidazo[4,5-b]pyridin-4-yl)methyl]-3-methoxybenzoic acid, N-2-butyl-N-cyclohexyl amide;

4-[(2-(hydroxymethyl)-4H-imidazo[4,5-b]pyridin-4-yl)methyl]-3-methoxybenzoic acid, N-phenyl-N-cyclohexyl amide;

4-[(2-(hydroxymethyl)-4H-imidazo[4,5-b]pyridin-4-yl)methyl]-3-methoxybenzoic acid, N-3-pentyl-N-cyclohexyl amide;

4-[(2-(hydroxymethyl)-4H-imidazo[4,5-b]pyridin-4-yl)methyl]-3-methoxybenzoic acid, N-3-methylcyclohexyl-N-cyclopentyl amide;

4-[(2-(hydroxymethyl)-4H-imidazo[4,5-b]pyridin-4-yl)methyl]-3-methoxybenzoic acid, N-4-methylcyclohexyl-N-cyclopentyl amide;

4-[(2-(hydroxymethyl)-4H-imidazo[4,5-b]pyridin-4-yl)methyl]-3-methoxybenzoic acid, N-2-methylcyclohexyl-N-cyclopentyl amide;

4-[(2-(hydroxymethyl)-4H-imidazo[4,5-b]pyridin-4-yl)methyl]-3-methoxybenzoic acid, N-2-methylcyclohexyl-N-isopropyl amide;

4-[(2-(hydroxymethyl) 4H-imidazo[4,5-b]pyridin-4-yl)methyl]-3-methoxybenzoic acid, N-3-methylcyclohexyl-N-isopropyl amide;

4-[(2-(hydroxymethyl)-4H-imidazo[4,5-b]pyridin-4-yl)methyl]-3-methoxybenzoic acid, N-3,5-dimethylcyclohexyl-N-isopropyl amide;

4-[(2-(methoxyoxymethyl)-4H-imidazo[4,5-b]pyridin-4-yl)methyl]-3-methoxybenzoic acid, N-cyclobutyl-N-cyclohexyl amide;

4-[(2-(methoxyoxymethyl)-4H-imidazo[4,5-b]pyridin-4-methyl]-3-methoxybenzoic acid, N-cyclopropyl-N-cyclohexyl amide;

4-[(2-(methoxyoxymethyl)-4H-imidazo[4,5-b]pyridin-4-yl)methyl]-3-methoxybenzoic acid, N-cyclopentyl-N-cyclopentyl amide;

4-[(2-(methoxyoxymethyl)-4H-imidazo[4,5-b]pyridin-4-yl)methyl]-3-methoxybenzoic acid, N-isopropyl-N-cyclopentyl amide;

4-[(2-(methoxyoxymethyl)-4H-imidazo[4,5-b]pyridin-4-yl)methyl]-3-methoxybenzoic acid, N-cyclohexyl-N-cyclohexyl amide;

4-[(2-(methoxyoxymethyl)-4H-imidazo[4,5-b]pyridin-4-yl)methyl]-3-methoxybenzoic acid, N-2-butyl-N-cyclohexyl amide;

4-[(2-(methoxyoxymethyl)-4H-imidazo[4,5-b]pyridin-4-yl)methyl]-3-methoxybenzoic acid, N-phenyl-N-cyclohexyl amide;

4-[(2-(methoxyoxymethyl)-4H-imidazo[4,5-b]pyridin-4-yl)methyl]-3-methoxybenzoic acid, N-3-pentyl-N-cyclohexyl amide;

4-[(2-(methoxyoxymethyl)-4H-imidazo[4,5-b]pyridin-4-yl)methyl]-3-methoxybenzoic acid, N-3-methylcyclohexyl-N-cyclopentyl amide;

4-[(2-(methoxyoxymethyl)-4H-imidazo[4,5-b]pyridin-4-yl)methyl]-3-methoxybenzoic acid, N-4-methylcyclohexyl-N-cyclopentyl amide;

4-[(2-(methoxyoxymethyl)-4H-imidazo[4,5-b]pyridin-4-yl)methyl]-3-methoxybenzoic acid, N-2-methylcyclohexyl-N-cyclopentyl amide;

4-[(2-(methoxyoxymethyl)-4H-imidazo[4,5-b]pyridin-4-yl)methyl]-3-methoxybenzoic acid, N-2-methylcyclohexyl-N-isopropyl amide;

4-[(2-(methoxyoxymethyl)-4H-imidazo[4,5-b]pyridin-4-yl)methyl]-3-methoxybenzoic acid, N-3-methylcyclohexyl-N-isopropyl amide;

4-[(2-(methoxyoxymethyl)-4H-imidazo[4,5-b]pyridin-4-yl)methyl]-3-methoxybenzoic acid, N-3,5-dimethylcyclohexyl-N-isopropyl amide;

4-[(2-(dimethylaminomethyl)-4H-imidazo[4,5-b]pyridin-4-yl)methyl]-3-methoxybenzoic acid, N-cyclobutyl-N-cyclohexyl amide;

4-[(2-(dimethylaminomethyl)-4H-imidazo[4,5-b]pyridin-4-yl)methyl]-3-methoxybenzoic acid, N-cyclopropyl-N-cyclohexyl amide;

4-[(2-(dimethylaminomethyl)-4H-imidazo[4,5-b]pyridin-4-yl)methyl]-3-methoxybenzoic acid, N-cyclopentyl-N-cyclopentyl amide;

4-[(2-(dimethylaminomethyl)-4H-imidazo[4,5-b]pyridin-4-yl)methyl]-3-methoxybenzoic acid, N-isopropyl-N-cyclopentyl amide;

4-[(2-(dimethylaminomethyl)-4H-imidazo[4,5-b]pyridin-4-yl)methyl]-3-methoxybenzoic acid, N-cyclohexyl-N-cyclohexyl amide;

4-[(2-(dimethylaminomethyl)-4H-imidazo[4,5-b]pyridin-4-yl)methyl]-3-methoxybenzoic acid, N 2 butyl-N-cyclohexyl amide;

4-[(2-(dimethylaminomethyl)-4H-imidazo[4,5-b]pyridin-4-yl)methyl]-3-methoxybenzoic acid, N-phenyl-N-cyclohexyl amide;

4-[(2-(dimethylaminomethyl)-4H-imidazo[4,5-b]pyridin-4-yl)methyl]-3-methoxybenzoic acid, N-3-pentyl-N-cyclohexyl amide;

4-[(2-(dimethylaminomethyl)-4H-imidazo[4,5-b]pyridin-4-yl)methyl]-3-methoxybenzoic acid, N-3-methylcyclohexyl-N-cyclopentyl amide;

4-[(2-(dimethylaminomethyl)-4H-imidazo[4,5-b]pyridin-4-yl)methyl]-3-methoxybenzoic acid, N-4-methylcyclohexyl-N-cyclopentyl amide;

4-[(2-(dimethylaminomethyl)-4H-imidazo[4,5-b]pyridin-4-yl)methyl]-3-methoxybenzoic acid, N-2-methylcyclohexyl-N-cyclopentyl amide;

4-[(2-(dimethylaminomethyl)-4H-imidazo[4,5-b]pyridin-4-yl)methyl]-3-methoxybenzoic acid, N 2-methylcyclohexyl-N-isopropyl amide;

4-[(2-(dimethylaminomethyl)-4H-imidazo[4,5-b]pyridin-4-yl)methyl]-3-methoxybenzoic acid, N-3-methylcyclohexyl-N-isopropyl amide;

4-[(2-(dimethylaminomethyl)-4H-imidazo[4,5-b]pyridin-4-yl)methyl]-3-methoxybenzoic acid, N-3,5-dimethylcyclohexyl-N-isopropyl amide;

4-[(2-(dimethylamino)-4H-imidazo[4,5-b]pyridin-4-yl)methyl]-3-methoxybenzoic acid, N-cyclobutyl-N-cyclohexyl amide;

4-[(2-(dimethylamino)-4H-imidazo[4,5-b]pyridin-4-yl)methyl]-3-methoxybenzoic acid, N-cyclopropyl-N-cyclohexyl amide;

4-[(2-(dimethylamino)-4H-imidazo[4,5-b]pyridin-4-yl)methyl]-3-methoxybenzoic acid, N-cyclopentyl-N-cyclopentyl amide;

4-[(2-(dimethylamino)-4H-imidazo[4,5-b]pyridin-4-yl)methyl]-3-methoxybenzoic acid, N-isopropyl-N-cyclopentyl amide;

4-[(2-(dimethylamino)-4H-imidazo[4,5-b]pyridin-4-yl)methyl]-3-methoxybenzoic acid, N-cyclohexyl-N-cyclohexyl amide;

4-[(2-(dimethylamino)-4H-imidazo[4,5-b]pyridin-4-yl)methyl]-3-methoxybenzoic acid, N-2-butyl-N-cyclohexyl amide;

4-[(2-(dimethylamino)-4H-imidazo[4,5-b]pyridin-4-yl)methyl]-3-methoxybenzoic acid, N-phenyl-N-cyclohexyl amide;

4-[(2-(dimethylamino)-4H-imidazo[4,5-b]pyridin-4-yl)methyl]-3-methoxybenzoic acid, N-3-pentyl-N-cyclohexyl amide;

4-[(2-(dimethylamino)-4H-imidazo[4,5-b]pyridin-4-yl)methyl]-3-methoxybenzoic acid, N-3-methylcyclohexyl-N-cyclopentyl amide;

4-[(2-(dimethylamino)-4H-imidazo[4,5-b]pyridin-4-yl)methyl]-3-methoxybenzoic acid, N 4-methylcyclohexyl-N-cyclopentyl amide;

4-[(2-(dimethylamino)-4H-imidazo[4,5-b]pyridin-4-yl)methyl]-3-methoxybenzoic acid, N-2-methylcyclohexyl-N-cyclopentyl amide;

4-[(2-(dimethylamino)-4H-imidazo[4,5-b]pyridin-4-yl)methyl]-3-methoxybenzoic acid, N-2-methylcyclohexyl-N-isopropyl amide;

4-[(2-(dimethylamino)-4H-imidazo[4,5-b]pyridin-4-yl)methyl]-3-methoxybenzoic acid, N-3-methylcyclohexyl-N-isopropyl amide;

4-[(2-(dimethylamino)-4H-imidazo[4,5-b]pyridin-4-yl)methyl]-3-methoxybenzoic acid, N-3,5-dimethylcyclohexyl-N-isopropyl amide;

4-[(2-(hydroxymethyl)-4H-imidazo[4,5-b]pyridin-4-yl)methyl]-2-methoxybenzoic acid, N-cyclobutyl-N-cyclohexyl amide;

4-[(2-(hydroxymethyl)-4H-imidazo[4,5-b]pyridin-4-yl)methyl]-2-methoxybenzoic acid, N-cyclopropyl-N-cyclohexyl amide;

4-[(2-(hydroxymethyl)-4H-imidazo[4,5-b]pyridin-4-yl)methyl]-2-methoxybenzoic acid, N-cyclopentyl-N-cyclopentyl amide;

4-[(2-(hydroxymethyl)-4H-imidazo[4,5-b]pyridin-4-yl)methyl]-2-methoxybenzoic acid, N-isopropyl-N-cyclopentyl amide;

4-[(2-(hydroxymethyl)-4H-imidazo[4,5-b]pyridin-4-yl)methyl]-2-methoxybenzoic acid, N-cyclohexyl-N-cyclohexyl amide;

4-[(2-(hydroxymethyl)-4H-imidazo[4,5-b]pyridin-4-yl)methyl]-2-methoxybenzoic acid, N-2-butyl-N-cyclohexyl amide;

4-[(2-(hydroxymethyl)-4H-imidazo[4,5-b]pyridin-4-yl)methyl]-2-methoxybenzoic acid, N-phenyl N-cyclohexyl amide;

4-[(2-(hydroxymethyl)-4H-imidazo[4,5-b]pyridin-4-yl)methyl]-2-methoxybenzoic acid, N-3-pentyl-N-cyclohexyl amide;

4-[(2-(hydroxymethyl)-4H-imidazo[4,5-b]pyridin-4-yl)methyl]-2-methoxybenzoic acid, N-3-methylcyclohexyl-N-cyclopentyl amide;

4-[(2-(hydroxymethyl)-4H-imidazo[4,5-b]pyridin-4-yl)methyl]-2-methoxybenzoic acid, N-4-methylcyclohexyl-N-cyclopentyl amide;

4-[(2-(hydroxymethyl)-4H-imidazo[4,5-b]pyridin-4-yl)methyl]-2-methoxybenzoic acid, N-2-methylcyclohexyl-N-cyclopentyl amide;

4-[(2-(hydroxymethyl)-4H-imidazo[4,5-b]pyridin-4-yl)methyl]-2-methoxybenzoic acid, N-2-methylcyclohexyl-N-isopropyl amide;

4-[(2-(hydroxymethyl)-4H-imidazo[4,5-b]pyridin-4-yl)methyl]-2-methoxybenzoic acid, N-3-methylcyclohexyl-N-isopropyl amide;

4-[2-(hydroxymethyl)-4H-imidazo[4,5-b]pyridin-4-yl)methyl]-2-methoxybenzoic acid, N-3,5-dimethylcyclohexyl-N-isopropyl amide;

4-[(2-(methoxyoxymethyl)-4H-imidazo[4,5-b]pyridin-4-yl)methyl]-2-methoxybenzoic acid, N-cyclobutyl-N-cyclohexyl amide;

4-[(2-(methoxyoxymethyl)-4H-imidazo[4,5-b]pyridin-4-yl)methyl]-2-methoxybenzoic acid, N-cyclopropyl-N-cyclohexyl amide;

4-[(2-(methoxyoxymethyl)-4H-imidazo[4,5-b]pyridin-4-yl)methyl]-2-methoxybenzoic acid, N-cyclopentyl-N-cyclopentyl amide;

4-[(2-(methoxyoxymethyl)-4H-imidazo[4,5-b]pyridin-4-yl)methyl]-2-methoxybenzoic acid, N-isopropyl-N-cyclopentyl amide; 4-[(2-(methoxyoxymethyl)-4H-imidazo[4,5-b]pyridin-4-yl)methyl]-2-methoxybenzoic acid, N-cyclohexyl-N-cyclohexyl amide;

4-[(2-(methoxyoxymethyl)-4H-imidazo[4,5-b]pyridin-4-yl)methyl]-2-methoxybenzoic acid, N-2-butyl-N-cyclohexyl amide;

4-[(2-(methoxyoxymethyl)-4H-imidazo[4,5-b]pyridin-4-yl)methyl]-2-methoxybenzoic acid, N-phenyl-N-cyclohexyl amide;

4-[(2-(methoxyoxymethyl)-4H-imidazo[4,5-b]pyridin-4-yl)methyl]-2-methoxybenzoic acid, N-3-pentyl-N-cyclohexyl amide;

4-[(2-(methoxyoxymethyl)-4H-imidazo[4,5-b]pyridin-4-yl)methyl]-2-methoxybenzoic acid, N-3-methylcyclohexyl-N-cyclopentyl amide;

4-[(2 (methoxyoxymethyl)-4H-imidazo[4,5-b]pyridin 4-yl)methyl]-2-methoxybenzoic acid, N-4-methylcyclohexyl-N-cyclopentyl amide;

4-[(2-(methoxyoxymethyl)-4H-imidazo[4,5-b]pyridin-4-yl)methyl]-2-methoxybenzoic acid, N-2-methylcyclohexyl, N-cyclopentyl amide;

4-[(2-(methoxyoxymethyl)-4H-imidazo[4,5-b]pyridin-4-yl)methyl]-2-methoxybenzoic acid, N-2-methylcyclohexyl-N-isopropyl amide;

4-[(2-(methoxyoxymethyl)-4H-imidazo[4,5-b]pyridin-4-yl)methyl]-2-methoxybenzoic acid, N-3-methylcyclohexyl-N-isopropyl amide;

4-[(2 (methoxyoxymethyl)-4H-imidazo[4,5-b]pyridin-4-yl)methyl]-2-methoxybenzoic acid, N-3,5-dimethylcyclohexyl-N-isopropyl amide;

4-[(2-(dimethylaminomethyl)-4H-imidazo[4,5-b]pyridin-4-yl)methyl]-2-methoxybenzoic acid, N-cyclobutyl-N-cyclohexyl amide;

4-[(2-(dimethylaminomethyl)-4H-imidazo[4,5-b]pyridin-4-yl)methyl]-2-methoxybenzoic acid, N-cyclopropyl-N-cyclohexyl amide;

4-[(2-(dimethylaminomethyl)-4H-imidazo[4,5-b]pyridin-4-yl)methyl]-2-methoxybenzoic acid, N-cyclopentyl-N-cyclopentyl amide;

4-[(2-(dimethylaminomethyl)-4H-imidazo[4,5-b]pyridin-4-yl)methyl]-2-methoxybenzoic acid, N-isopropyl-N-cyclopentyl amide;

4-[(2-(dimethylaminomethyl)-4H-imidazo[4,5-b]pyridin-4-yl)methyl]-2-methoxybenzoic acid, N-cyclohexyl-N-cyclohexyl amide;

4-[(2-(dimethylaminomethyl)-4H-imidazo[4,5-b]pyridin-4-yl)methyl]-2-methoxybenzoic acid, N-2-butyl-N-cyclohexyl amide;

4-[(2-(dimethylaminomethyl)-4H-imidazo[4,5-b]pyridin-4-yl)methyl]-2-methoxybenzoic acid, N-phenyl-N-cyclohexyl amide;

4-[(2-(dimethylaminomethyl)-4H-imidazo[4,5-b]pyridin-4-yl)methyl]-2-methoxybenzoic acid, N-3-phenyl-N-cyclohexyl amide;

4-[(2-(dimethylaminomethyl)-4H-imidazo[4,5-b]pyridin-4-yl)methyl]-2-methoxybenzoic acid, N-3-methylcyclohexyl-N-cyclopentyl amide;

4-[(2-(dimethylaminomethyl)-4H-imidazo[4,5-b]pyridin-4-yl)methyl]-2-methoxybenzoic acid, N-4-methylcyclohexyl-N-cyclopentyl amide;

4-[(2-(dimethylaminomethyl)-4H-imidazo[4,5-b]pyridin-4-yl)methyl]-2-methoxybenzoic acid, N-2-methylcyclohexyl-N-cyclopentyl amide;

4 [(2-(dimethylaminomethyl)-4H-imidazo[4,5-b]pyridin-4-yl)methyl]-2-methoxybenzoic acid, N-2-methylcyclohexyl-N-isopropyl amide;

4-[(2-(dimethylaminomethyl)-4H-imidazo[4,5-b]pyridin-4-yl)methyl]-2-methoxybenzoic acid, N-3-methylcyclohexyl-N-isopropyl amide;

4-[(2-(dimethylaminomethyl)-4H-imidazo[4,5-b]pyridin-4-yl)methyl]-2-methoxybenzoic acid, N-3,5-dimethylcyclohexyl-N-isopropyl amide;

4-[(2-(dimethylamino)-4H-imidazo[4,5-b]pyridin-4-yl)methyl]-2-methoxybenzoic acid, N-cyclobutyl-N-cyclohexyl amide;

4-[(2-(dimethylamino)-4H-imidazo[4,5-b]pyridin-4-cyclohexyl amide;

4-[(2-(dimethylamino)-4H-imidazo[4,5-b]pyridin-4-yl)methyl]-2-methoxybenzoic acid, N-cyclopentyl-N-cyclopentyl amide;

4-[(2-(dimethylamino)-4H-imidazo[4,5-b]pyridin-4-yl)methyl]-2-methoxybenzoic acid, N-isopropyl-N-cyclopentyl amide;

4-[(2-(dimethylamino)-4H-imidazo[4,5-b]pyridin-4-yl)methyl]-2-methoxybenzoic acid, N-cyclohexyl-N-cyclohexyl amide;

4-[(2-(dimethylamino)-4H-imidazo[4,5-b]pyridin-4-yl)methyl]-2-methoxybenzoic acid, N-2-butyl-N-cyclohexyl amide;

4-[(2-(dimethylamino)-4H-imidazo[4,5-b]pyridin-4-yl)methyl]-2-methoxybenzoic acid, N-phenyl-N-cyclohexyl amide;

4-[(2-(dimethylamino)-4H-imidazo[4,5-b]pyridin-4-yl)methyl]-2-methoxybenzoic acid, N-3-pentyl-N-cyclohexyl amide;

4-[(2-(dimethylamino)-4H-imidazo[4,5-b]pyridin-4-yl)methyl]-2-methoxybenzoic acid, N-3-methylcyclohexyl-N-cyclopentyl amide;

4-[(2-(dimethylamino)-4H-imidazo[4,5-b]pyridin-4-yl)methyl]-2-methoxybenzoic acid, N-4-methylcyclohexyl-N-cyclopentyl amide;

4-[(2-(dimethylamino)-4H-imidazo[4,5-b]pyridin-4-yl)methyl]-2-methoxybenzoic acid, N-2-methylcyclohexyl-N-cyclopentyl amide;

4-[(2-(dimethylamino)-4H-imidazo[4,5-b]pyridin-4-yl)methyl]-2-methoxybenzoic acid, N-2-methylcyclohexyl-N-isopropyl amide;

4-[(2-(dimethylamino)-4H-imidazo[4,5-b]pyridin-4-yl)methyl]-2-methoxybenzoic acid, N-3-methylcyclohexyl-N-isopropyl amide; and 4-[(2-(dimethylamino)-4H-imidazo[4,5-b]pyridin-4-yl)methyl]-2-methoxybenzoic acid, N-3,5-dimethylcyclohexyl-N-isopropyl amide.

General Synthetic Procedures

Compounds of Formula I may be prepared in accordance with the general procedure shown below:

Step (a): Preparation of 1H-Imidazo[4,5-b]pyridine Compounds

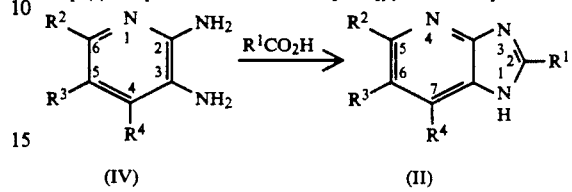

Step (b): Preparation of Formula I Compounds

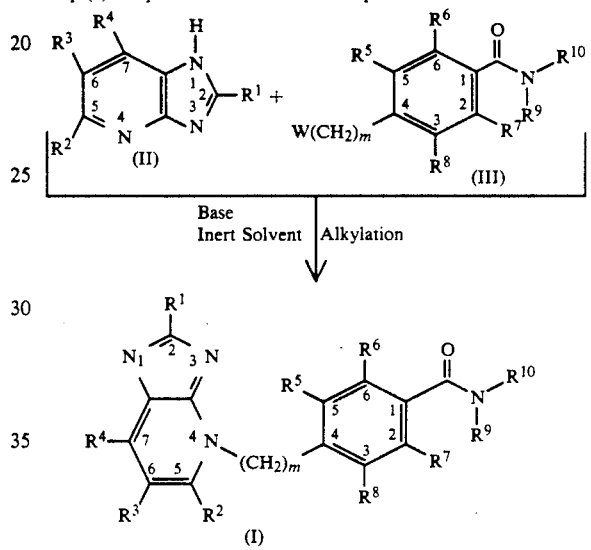

wherein m, $R^1$–$R^{10}$ are defined above and W is selected from halo, alkylsulfonyloxy and arylsulfonyloxy.

Step (a), in the scheme above, shows a general procedure for synthesizing 1H-imidazo[4,5-b]pyridine compounds which are intermediates for use in Step (b). Synthesis of imidazopyridines (II) may be carried out by reacting a 2,3-diaminopyridine (IV) with a substituted carboxylic acid ($R^1CO_2H$) or a carboxylic acid equivalent such as a trialkyl orthoformate [$R^1C(OR)_3$ wherein R is any lower alkyl group such as methyl or ethyl]. The reaction of (IV) with a carboxylic acid derivative ($R^1CO_2H$) may be carried out by heating at higher temperature with or without the presence of an acid such as polyphosphoric acid. The reaction of (IV) with a trialkyl orthoformate may be carried out in the presence of an acid catalyst such as p-toluenesulfonic acid. Step (b), in the scheme above, shows a general procedure for reacting intermediate (II) from Step (a) with a benzylic bromide (III) to form compounds of Formula I. An appropriate benzylic bromide (III) may be synthesized by the methods shown in U.S. Pat. No. 5,019,581 and No. 4,962,106. Compounds of Formula I are prepared by alkylating an appropriately-substituted imidazo[4,5-b]pyridine (II) with an appropriate benzylic bromide (III). This reaction may be carried out in a polar solvent with or without the presence of a base. Suitable solvents for this reaction are, for example, N,N-dimethylformamide, N,N-dimethylacetamide, dimethylsulfoxide, N-methylpyrrolidinone, acetonitrile, tetrahydrofuran, acetone and the like. Non-nucleophilic bases useful in this reaction are, for example, sodium hydride, cesium carbonate, potassium carbonate, sodium carbonate, 1,8-diazabicyclo[5.4.0]undec-7-ene, N,N-diisopropylethylamine, triethylamine and the like. This alkylation reaction may be carried out at a temperature of about 20° C. to 110° C.

The following Examples 1-9 are detailed descriptions of the synthetic steps for preparing compounds of the invention. These detailed preparations fall within the scope of, and serve to exemplify, the more generally described procedures above. These Examples 1-8 are presented for illustrative purposes only and are not intended as a restriction on the scope of the invention. Most of the commercially-available materials were obtained from Aldrich Chemical Co., Milwaukee, Wis.

EXAMPLE 1

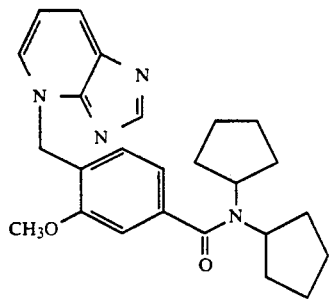

N,N-dicyclopentyl-4-[(4H-imidazo[4,5-b]pyridin-4-yl)methyl]-3-methoxybenzamide

To a stirred solution of imidazo[4,5-b]pyridine (350 mg, 2.94 mmol) in N,N-dimethylformamide (25 mL), sodium hydride (118 mg, 60% dispersion in mineral oil, 2.94 mmol) was added. After stirring for 2 hr, 4-bromomethyl-3-methoxy-N,N-dicyclopentyl benzamide (1.4 g, 3.57 mmol) was added in small installments over 10 min. The reaction mixture was stirred under argon at 25° C. After 18h, the reaction was quenched by adding acetic acid (0.5 mL) and the solvent was removed under reduced pressure at <45° C. The crude mixture (2 g) was chromatographed (silica gel, $CH_2Cl_2$-MeOH-$NH_4OH$ 90-10-1) to give the title compound. (145 mg, 12%) mp 223°-224° C.; Anal calcd. for $C_{25}H_{30}N_4O_2 \cdot 1.0H_2O$: C, 68.78; H, 7.39; N, 12.83. Found C, 68.88; H, 7.13; N, 12.55.

EXAMPLE 2

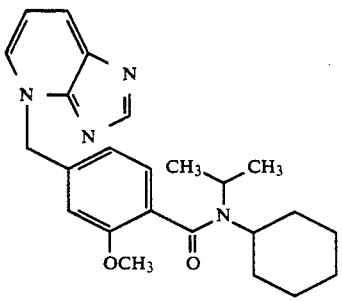

N-cyclohexyl-4-[(4H-imidazo[4,5-b]pyridin-4-yl)methyl]-2-methoxy-N-(1-methylethyl)benzamide To a stirred solution of imidazo[4,5-b]pyridine (350 mg, 2.94 mmol) in N,N-dimethylformamide (25 mL), sodium hydride (118 mg, 60% dispersion in mineral oil, 2.94 mmol) was added. After stirring for 2 hr, 4-bromomethyl-2-methoxy-N-isopropyl,N-cyclohexyl benzamide (1.07 g, 2.94 mmol) was added over 10 min. The reaction mixture was stirred under argon at 25° C. After 18h, the reaction was quenched by adding acetic acid (0.5 mL) and the solvent was removed under reduced pressure at <45° C. The crude mixture (1.6 g) was chromatographed (silica gel, $CH_2Cl_2$-MeOH-$NH_4OH$ 90-10-1) to give the title compound. (243 mg, 23%) mp 98°-100° C.; Anal calcd. for $C_{24}H_{30}N_4O_2 \cdot 0.8 H_2O$: C, 68.48; H, 7.57; N, 13.31. Found C, 68.47; H, 7.52; N, 12.81.

EXAMPLE 3

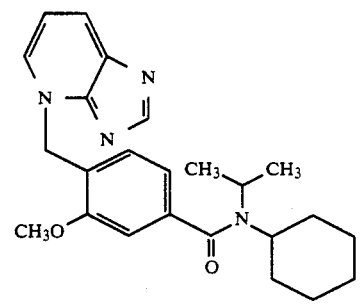

N-cyclohexyl-4-[(4H-imidazo[4,5-b]pyridin-4-yl)methyl]-3-methoxy-N-(1-methylethyl)benzamide

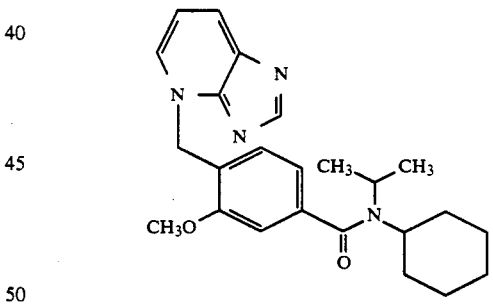

Preparation A:

To a stirred solution of imidazo[4,5-b]pyridine (200 mg, 1.68 mmol) in N,N-dimethylformamide (40 mL), 4-bromomethyl-3-methoxy-N-isopropyl,N-cyclohexyl benzamide (0.59 g, 1.68 mmol) was added. The reaction mixture was stirred under argon at 25° C. After 72 h, the solvent was removed under reduced pressure at <45° C. The crude mixture (1.58 g) was chromatographed (silica gel, $CH_2Cl_2$-MeOH-$NH_4OH$ 95-5-0 5) to give pure title compound (320 mg, 47%) DSC 230° C. Anal calcd. for $C_{24}H_{30}N_4O_2$: C, 70.91; H, 7.44; N, 13.78 Found C, 70.58; H, 7.55; N, 13.57.

Preparation B:

To a stirred solution of imidazo[4,5-b]pyridine (350 mg, 2.94 mmol) in N,N-dimethylformamide (25 mL), sodium hydride (120 mg, 60% dispersion in mineral oil, 2.94 mmol) was added. After stirring for 2 hr, 4-bromomethyl-3-methoxy-N-isopropyl,N-cyclohexyl benzamide (1.07 g, 2.94 mmol) was added over 15 min. The reaction mixture was stirred under argon at 25° C. After 18 h, the reaction was quenched by adding acetic acid (0.5 mL) and the solvent was removed under reduced pressure at <45° C. The crude mixture (1.58 g) was chromatographed (silica gel, $CH_2Cl_2$-MeOH-$NH_4OH$ 90-10-1) to give the title compound. (150 mg, 13%) $^1H$ NMR ($CD_3OD$) 8.35 (m, 2H), 8.22 (d, J=7 Hz, 1H), 7.32 (m, 2H), 6.97 (d, J=2 Hz, 1H), 6.86 (dd, J=7, 2 Hz, 1H), 5.93 (s, 2H), 3.87 (s, 3H), 3.68 & 3.33 (complex band, 1H), 3.12 & 2.57 (complex band, 1H), 0.9-1.9 (m, 16H).

EXAMPLE 4

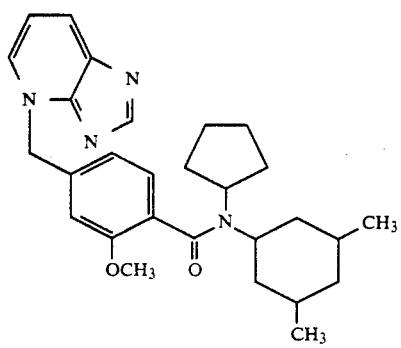

N-cyclopentyl-N-(3,5-dimethylcyclohexyl)-4-[(4H-imidazo[4,5-b]pyridin-4-yl)methyl]-2-methoxybenzamide To a stirred solution of imidazo[4,5-b]pyridine (220 mg, 1.84 mmol) in N,N-dimethylformamide (20 mL), sodium hydride (74 mg, 60% dispersion in mineral oil, 1.85 mmol) was added. After stirring for 2 hr, 4-bromomethyl-2-methoxy-N-cyclopentyl,N-3,5-dimethylcyclohexyl benzamide (740 mg, 2.94 mmol) was added over 15 min. The reaction mixture was stirred under argon at 25° C. After 18 h, the reaction was quenched by adding acetic acid (1 mL) and the solvent was removed under reduced pressure at <45° C. The crude mixture (1.2 g) was chromatographed (silica gel, $CH_2Cl_2$-MeOH-$NH_4OH$ 95-5-0.5) to give the title compound (168 mg, 20%) DSC 202° C. Anal calcd. for $C_{28}H_{36}N_4O_2 \cdot 0.25H_2O$: C, 72.31; H, 7.91; N, 12.05. Found C, 72.36; H, 7.98; N, 11.95.

EXAMPLE 5

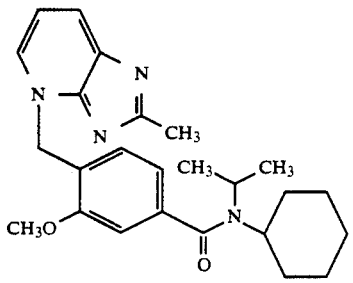

N-cyclohexyl-3-methoxy-N-(1-methylethyl)-4-[(2-methyl-4H-imidazo[4,5-b]pyridin-4-yl)methyl]benzamide 2-Methyl-1(H)-imidazo[4,5-b]pyridine (1.3 g, 0.010 mol) was stirred with cesium carbonate (3.5 g) in DMF (20 mL) at 60° C. for 2 hours under an argon atmosphere. A solution of 4-bromomethyl-3-methoxy-N-isopropyl, N-cyclohexyl benzamide (3.72 g) in DMF (20 mL) was added and the reaction stirred at 60° C. for 2 hours. The insoluble material was filtered and the reaction concentrated in vacuo on a rotary evaporator using an oil pump. The residue was treated with ethyl acetate and water and the organic layer was dried ($Na_2SO_4$). The drying agent was filtered and the filtrate concentrated in vacuo. The residue was chromatographed on silica gel using mixtures of $CH_2Cl_2$, MeOH and ammonium hydroxide to give the title compound (900 mg, 21%) m.p. 218°-221° C. $C_{25}H_{32}N_4O_2 \cdot 1H_2O$ Calc: C, 68.47; H, 7.81; N, 12.77. Found: C, 68.54; H, 7.82; N, 12.42.

EXAMPLE 6

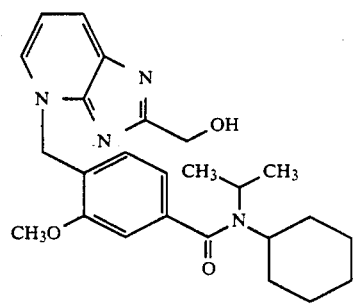

N-cyclohexyl-4-[[2-(hydroxymethyl)-4H-imidazo[4,5-b]pyridin-4-yl]methyl]-3 methoxy-N-(1-methylethyl)benzamide Step (a): Preparation of silyl ether intermediate shown below

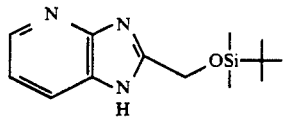

A solution of 2-hydroxymethyl-1(H)-imidazo[4,5-b]pyridine (1.0 g, 6.7 mmol), tert.-butyldimethylsilyl chloride (1.1 g, 7.3 mmol) and imidazole (460 mg, 6.76 mmol) in dimethylformamide (10 mL) was stirred for 3 hr. at room temperature under an argon atmosphere. The reaction solvent was removed in vacuo using an oil pump. Dilute ammonium hydroxide was added to the residue and the resulting solid was filtered and air dried to give the pure title compound: m.p. 155°-156°. $^1H$ NMR (300 MHz, $CD_3OD$, ppm): 0.15 (s, 6H, $CH_3$); 0.95 (s, 9H, $(CH_3)_3$); 5.00 (s, 2H, benzylic); 7.30 (dd, 1H, J=5 Hz, H6 of pyridine); 8.00 (d, 1H, J=5 Hz, H7 of pyridine); 8.35 (d, 1H, J=5 Hz, H5 of pyridine). Anal. Calcd. for $C_{13}H_{21}N_3OSi$: C, 59.28; H, 8.04; N, 15.95. Found: C, 59.11; H, 8.25; N, 15.72.

Step (b): Preparation of silyl ether imidazo[4,5-b]pyridine compound shown below

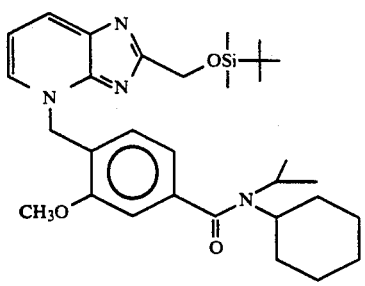

The silyl ether synthesized in Step (a), above, (1.75 g, 6.0 mmol) was added portionwise to a stirred slurry of NaH (prepared by washing 250 mg or 6.25 mmol of a 60% dispersion in silicone oil) in dimethylacetamide (15 mL) under a nitrogen atmosphere. After stirring for 15 min. at room temperature, 4-bromomethyl-3-methoxybenzoic acid N-isopropyl-N-cyclohexylamide (2.2 g) was added and the reaction stirred at room temperature overnight. The solvent was removed in vacuo using an oil pump and the residue treated with methylene chloride and dilute $NH_4OH$. The layers were separated and the aqueous was extracted with methylene chloride. The combined organic layers were dried ($Na_2SO_4$), filtered and the filtrate concentrated in vacuo to give the crude product. Pure title compound was obtained by chromatography of the crude product on silica gel using mixtures of EtOAc, MeOH and $NH_4OH$, m.p. 133°–135°. $^1H$ NMR (300 MHz, $CDCl_3$, ppm): 0.15 ppm (s, 6H, dimethylsilyl); 0.85 (s, 9H, t-butyl); 3.85 (s, 3H, OMe); 5.00 (s, 2H, $OCH_2$); 5.50 (s, 2H, $CH_2Ph$); 6.62 and 6.68 (d, 1H each, J=8 Hz, H4 and H5 on phenyl); 6.85 (s, 1H, H3 on phenyl); 7.10, (dd, 1H, J=5 Hz, H6 on pyridine); 7.5 (d, 1H, J=5 Hz, H7 pyridine). Anal. Calcd. for $C_{31}H_{46}N_4O_3Si \cdot 0.5H_2O$: C, 66.51; H, 8.46; N, 10.01. Found: C, 66.59; H, 8.35; N, 10.00.

Step (c) Preparation of title compound

A solution of the silyl ether imidazo[4,5-b]-pyridine compound of Step (b) (1.0 g, 1.8 mmol) in tetrahydrofuran (THF) (10 mL) was treated with a solution of tetra-n-butyl ammonium fluoride (4 mL of a 1M solution in THF) with stirring for 3 hrs at room temperature. The reaction mixture was poured onto 5 mL of saturated aqueous $NaHCO_3$ solution and extracted twice with $CH_2Cl_2$. The combined organic layers were dried ($Na_2SO_4$), filtered and the filtrate concentrated in vacuo to give 800 mg (98%) of the crude product. Purification was effected by chromatography on silica gel using mixtures of EtOAc, MeOH and $NH_4OH$. The purified product was a crystalline solid, m.p. 134°–135°. The NMR (300 MHz, $CDCl_3$) is identical with the silyl ether except the $CH_2O$ singlet is shifted to 5.10 ppm and signals associated with the silyl ether are absent. Anal. Calcd for $C_{25}H_{32}N_4O_3 \cdot 0.75H_2O$: C, 66.72; H, 7.50; N, 12.45. Found: C, 66.42; H, 7.45; N, 12.20.

EXAMPLE 7

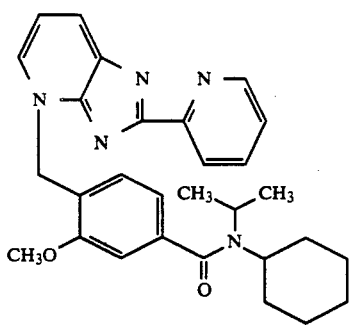

N-cyclohexyl-3-methoxy-N-(1-methylethyl)-4-[[2-(2-pyridinyl)-4H-imidazo[4,5-b]pyridin-4-yl]methyl]benzamide Step (a): Preparation of 2-(2-pyridyl)-1H-imidazo-(4,5-b)pyridine A solution of 2,3-diaminopyridine (1.1 g, 10 mmol) and 2-picolinic acid (1.23 g, 10 mmol) in polyphosphoric acid (10 ml) was heated to 160° C. for 4 hours. The hot solution was poured into ice water and the pH adjusted to pH 9 with conc. $NH_4OH$. The resulting precipitate was filtered and air dried. This crude product was recrystallized from EtOH to give 1.1 g (56%) of the title compound, m.p. 139°–142° C. Anal. Calcd for $C_{11}H_8N_4$: C, 67.34; H, 4.11; N, 28.36. Found: C, 66.88; H, 4.17; N, 8.36.

Step (b): Preparation of title compound 2-(2-Pyridyl)-1H-imidazo(4,5-b)pyridine (1.1 g, 5.6 mmol) was added portionwise with stirring over 5 minutes to a suspension of hexane-washed NaH (150 mg, 6.16 mmol) in dimethylacetamide (15 ml) under Ar and stirred at room temperature for 1 hour. 4-Bromomethyl-3-methoxy-N-cyclohexyl-N-isopropylbenzamide (2.1 g, 5.6 mmol) was added portionwise over 30 minutes and the mixture was stirred overnight at 25° C. The solvent was removed at <50° C. in vacuo using an oil pump and the residue was chromatographed on silica gel with 95/5/1 $CH_2Cl_2/MeOH/NH_4OH$ to give the titled product (1.95 g, 67%) as a glass. Anal. Calcd. for $C_{29}H_{33}N_5O_2 \cdot H_2O$: C, 69.44; H, 7.03; N, 13.96. Found: C, 69.70; H, 7.16; N, 13.87.

EXAMPLE 8

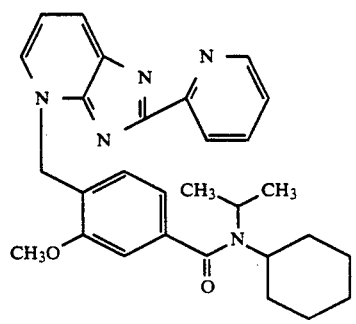

N-cyclohexyl-3-methoxy-N-(1-methylethyl)-4-[[2-(3-pyridinyl)-4H-imidazo[4,5-b]pyridin-4-yl]methyl]benzamide Step (a): Preparation of 2-(3-pyridyl)-1H-imidazo-(4,5-b)pyridine A solution of 2,3-diaminopyridine (1.1 g, 10 mmol) and nicotinic acid (1.23 g, 10 mmol) in polyphosphoric acid (15 mL) was heated at 160° C. for 4 hours and poured into 150 mLs of water. The pH was adjusted to pH 8 with NH4OH with cooling. The precipitate was filtered and air dried. Recrystallization from EtOH to give 1.3 g of product (66%), m.p.=133°-135° C. Anal. Calcd. for: C, 67.34; H, 4.11, N, 28.36. Found: C, 67.21; H, 4.04; N, 28.11.

Step (b): Preparation of title compound 2-(3-Pyridyl)-1H imidazo(4,5-b)pyridine (1.3 g, 6.6 mmol) was added to a hexane-washed suspension of NaH (175 mg, 7.26 mmol) in dimethylacetamide (15 ml) under Ar and stirred under an argon atomsphere for one hour at 25° C. 4-Bromomethyl-3-methoxy-N-cyclohexyl-N-isopropylbenzamide (2.5 g, 6.6 mmol) was added portionwise over 30 minutes and the mixture stirred overnight at 25° C. The solvent was removed via oil pump at <50° C. and the residue was chromatographed using 7/3/0.5 CH2Cl2/MeOH/NH4OH as the eluent to produce the title compound (1.70 g, 52%). An analytical sample was prepared by recrystallization from ethyl acetate, m.p. 185°-188° C. Anal. Calc. for $C_{29}H_{33}N_5O_2 \cdot 0.5H_2O$: C, 70.71; H, 6.96; N, 14.22. Found: C, 70.88; H, 6.80; N, 14.18.

EXAMPLE 9

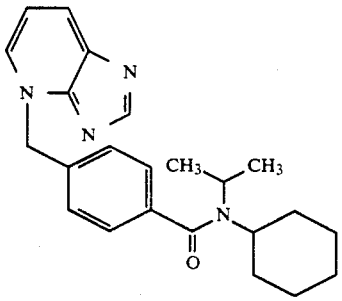

N-cyclohexyl-4-[(4H-imidazo[4,5-b]pyridin-4 yl)methyl]-N-(1-methylethyl)benzamide Procedure A A solution of 1(H)-imidazo[4,5-b]pyridine (300 mg, 2.52 mmol) and 4-chloromethylbenzoic acid N-isopropyl, N-cyclohexyl amide (370 mg, 1.26 mmol) in acetonitrile (11 ml) was stirred at room temperature overnight and then refluxed for 24 hrs. The reaction mixture was cooled and concentrated on the rotary evaporator to give a light brown solid. Purification of the crude product was effected by chromatography on silica gel using CH2CL2/MeOH/NH4OH (95/5/0.5) as the eluent to give 200 mg of pure title compound, m.p. 186°-187° C. Anal. Calcd. for $C_{23}H_{28}N_4O$: C, 73.37; H, 7.50; N, 14.88. Found: C, 73.07; H, 7.61; N, 14.81.

Procedure B

To a stirred solution of 1(H)-imidazo[4,5-b]pyridine (500 mg, 4.12 mmol) in dimethylformamide (15 mL) was added cesium carbonate (1.5 g, 4.62 mmol) and the resulting mixture was heated at 80° C. for 2 hrs. Then, 4-bromomethylbenzoic acid N-isopropyl,N-cyclohexyl amide (1.23 g, 4.12 mmol) was added and the heating continued at 80° C. for 3.5 hrs. The reaction was cooled, filtered and filtrate concentrated in vacuo on the rotary evaporator using an oil pump. The resulting crude product was purified by chromatography on silica gel using CH2Cl2/MeOH/NH4OH (97/3/0.1) as the eluent to give purified title compound.

Biological Evaluation

Assay A: Human Platelet Receptor Binding

Compounds of the invention were evaluated for their ability to inhibit specific binding of [$^3$H]PAF to human platelet membrane preparation. Human packed platelets were obtained from Lifesource, Inc. (Glenview, Ill.) and washed 3 times with 10 mM Trizma pH 7.0, 2 mM EDTA (dipotassium salt), 150 mM KCl and then once with 10 mM Trizma 7.4, 20 mM CaCl2. The platelets were broken by freezing in a dry ice-ethanol bath, followed by thawing in 24° C. water baths. The preparation was centrifuged (40,000 x g, 20 minutes, 4'C) and the pellet resuspended in 10 mM Trizma 7.4, 20 mM CaCl2, 5 mg/ml human albumin. Protein concentration in the platelet membrane preparation was determined by the Lowry method [0. H. Lowry et al, J. Biol. Chem., 193 265-275 (1951)]. Aliquots of the membrane preparation were stored at −70° C. Each preparation was characterized for PAF receptor number and dissociation constant (Kd). In binding assays 5 µl of test compound, solubilzed in DMSO, was added to polypropylene tubes along with 0.75 nM [$^3$H]PAF and 200 mcl [0.075 nM] of membranes and 95 µl 10 mM Trizma 7.4, 20 mM CaCL2, 5 mg/ml human albumin. Tubes were incubated for 30 minutes at 24° C. The incubation was terminated by adding 4 ml of ice-cold 10 mM Trizma pH 7.4, 20 mM CaCl2 and 20 mg/ml BSA prior to vacuum filtration using Whatman GF/C filters. Filters were prepared and counted for a scintillation counter. All DPM values were corrected for background and isotope decay. Triplicate determinations for single doses were averaged. The amount of non-specific binding was subtracted from all dose averages, giving an amount of specific binding in all cases. The IC50 values for compounds of the invention determined by the Allfit program using percent displacement data. Allfit is a "basic" computer program for simultaneous curve fitting of a family of sigmoidal dose-response curves using the four parameter logistic equation. Results are shown in Table I.

Assay B: Human Platelet Aggregation Inhibition

A compound of the invention was evaluated for ability to inhibit PAF-induced aggregation of human platelets in a human-platelet-rich plasma. Venous blood was collected from donors who fasted for 8 hours and were instructed not to use antiinflammatory drugs for 2 weeks prior to blood draw. Blood was collected into syringes containing 0.1 ml of 3.8% [w/v] citrate and centrifuged in polypropylene tubes at 150xg for 20 minutes at room temperature. The platelet rich plasma [PRP] was collected and let sit for 20 minutes at room temperature. Platelet activating factor [PAF] was diluted in 0.9% NaCl with 0.25% bovine serum albumin. Silicon treated cuvettes with stir bars were placed in the 37° heating block of the platelet aggregometer [Bio-Data Corporation, Platelet Aggregation Profiler, Model PAP-4]. PRP and test compound were added to cuvettes and aggregation monitored for 10–15 seconds at 37° with stirring. PAF was added and aggregation monitored for an additional 3 minutes. Peak aggregation was considered the peak of the first aggregation wave usually 45–60 seconds after PAF addition. Inhibition of aggregation was determined by the following: 1-[(% aggregation in the presence of compound)÷(% maximal aggregation)]. A log/logit transformation was used to determine half maximal inhibitory concentration of a test compound [$IC_{50}$]. Results are shown in Table I.

Assay C: Human Neutrophil Receptor Binding

Compounds of the invention can be evaluated for their ability to inhibit PAF-induced specific binding of [$^3$H]PAF to receptors on human neutrophil membrane by the following procedure. Human neutrophils are isolated from venous blood by dextran sedimentation followed by density gradient centrifugation using Ficoll-Hypaque [J. Biol. Chem., 254:7865–7869, 1979]. Residual red blood cells are removed by hypotonic lysis. Neutrophils are suspended in 50 mM Tris-HCl buffer, pH 7.7, and cells disrupted by sonication for 15 seconds on ice. Unbroken cells and nuclei are removed by slow speed centrifugation [1000 xg, 10 min. 4°]. The resultant supernatant is centrifuged at 100,000xg for 60 minutes at 4°. The pellet is suspended in 10 mM Tris-HCl, pH 7.4, with 10 mM $MgCl_2$. Protein content is determined by the method of Lowry [J. Biol. Chem., 193:265–275, 1951]. Membranes are characterized for the concentration of binding sites [Bmax] and affinity for the ligand [Kd] using [$^3$H]PAF by Scatchard analysis. Binding assays are conducted by incubating 50 mcg of membranes with 0.9 nM [$^3$H]PAF and test compound in 10 mM Tris-HCl buffer, pH 7.4, containing 0.1% bovine serum albumin. Nonspecific binding is determined by the addition of 1 µM PAF. The binding assay is carried out for 30 minutes at 24° C. The assay is terminated by filtration through a Whatman GF/C glass filter and radioactivity determined by liquid scintillation counting. Compounds of the invention would be expected to inhibit PAF-induced specific binding of [$^3$H]PAF to human neutrophil membrane receptors.

TABLE I

| Evaluation of PAF Antagonist Activity of Compounds of the Invention | | |
|---|---|---|
| Example # | Assay A[1] $IC_{50}$ (nM) | Assay B[2] $IC_{50}$ (nM) |
| 1 | 1051 | — |
| 2 | 40% inhibition at 10 µM | — |
| 3 | 643 | — |
| 4 | 139 | 58 |
| 5 | 323 | — |
| 6 | 460 | — |
| 7 | 732 | — |
| 8 | 68% inhibition @ 10 nM | — |
| 9 | 854 | — |

[1]Assay A: Human Platelet Receptor Binding
[2]Assay B: Human Platelet Aggregation Inhibition Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient in a range from about 1 to about 1000 mg, preferably from about 1 to about 500 mg, and more preferably from about 10 to about 100 mg. A suitable daily dose for a mammal may vary widely depending on the condition of the patient and other factors. However, a dose in a range from about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is in a range from about 0.1 to 100 mg/kg body weight injected per day in multiple doses depending on the disease being treated. A preferred daily dose would be from about 1 to 50 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These subdoses may be administered in unit dosage forms. Typically, a dose or sub-dose may contain from about 1 mg to about 1000 mg of active compound per unit dosage form. A more preferred dosage will contain from about 2 mg to about 500 mg of active compound per unit dosage form. Most preferred is a dosage form containing from about 3 mg to about 400 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered cer os. the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A compound of Formula I:

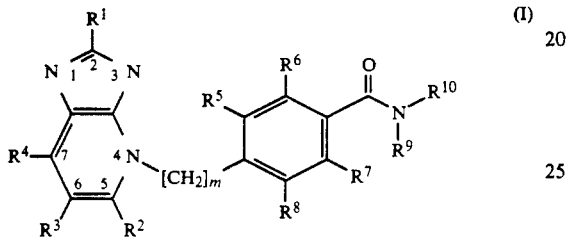

wherein m is a number selected from one through six, inclusive;

wherein $R^1$ is selected from hydrido, alkyl, hydroxyalkyl, formyl, halo, haloalkyl, cycloalkyl, alkylcycloalkyl, cycloalkylalkyl, cycloalkylhaloalkyl, cycloalkylcarbonyl, alkoxy, aralkyl, aralkylhaloalkyl, aryl, haloaryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, alkylsilyloxyalkyl, aryl/alkylsilyloxyalkyl, arylsilyloxyalkyl, mercaptoalkyl, alkoxycarbonyloxy, alkylthio, alkylthioalkyl, alkylsulfinylalkyl, alkylsulfonylalkyl, cycloalkylthio, cycloalkylalkylthio, alkylcarbonylthio, arylthio, arylcarbonylthio, aralkylthio, aralkylcarbonylthio, and heterocyclic and heterocyclicalkyl having one or more ring atoms selected from oxygel, sulfur and nitrogen atoms;

wherein each of $R^2$, $R^3$ and $R^4$ is independently selected from hydrido, alkyl, hydroxyalkyl, formyl, halo, haloalkyl, cycloalkyl, alkylcyc,loalkyl, cycloalkylalkyl, cycloalkylhaloalkyl, cycloalkylcarbonyl, alkoxy, aralkyl, aralkylhaloalkyl, alkoxyalkyl, alkylcarbonyl, alkylcarbonylalkyl, alkylsilyloxyalkyl, alkoxycarbonyl, cyano, nitro, alkylthio, alkylthioalkyl, alkylsulfinylalkyl, alkylsulfonylalkyl, cycloalkylthio and cycloalkylalkylthio;

wherein each of $R^5$, $R^6$, $R^7$ and $R^8$ is independently selected from hydrido, alkyl, hydroxy, hydroxyalkyl, formyl, halo, haloalkyl, cycloalkyl, alkylcycloalkyl, cycloalkylalkyl, cycloalkylhaloalkyl, cycloalkylcarbonyl, alkoxy, aralkyl, aralkylhaloalkyl, aryl, haloaryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, alkylsilyoxyalkyl, alkoxycarbonyloxy, alkylthio, alkylthioalkyl, alkylsulfinylalkyl, alkylsulfonylalkyl, cycloalkylthio, cycloalkylalkylthio, alkylcarbonylthio, arylthio, arylcarbonylthio, aralkylthio and aralkylcarbonylthio;

wherein each of $R^1$, $R^2$, $R^3$, $R^4$, $R^5$, $R^6$, $R^7$ and $R^8$ may be further independently selected from amino and amido radicals of the formulae

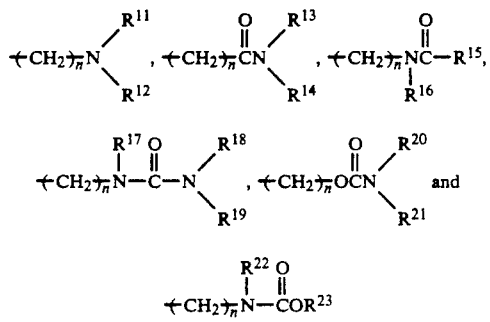

wherein each n is a number independently selected from zero to six, inclusive; wherein each of $R^{11}$ through $R^{23}$ is independently selected from hydrido, alkyl, cycloalkyl, hydroxyalkyl, cycloalkylalkyl, alkoxyalkyl, aralkyl and aryl;

wherein each of $R^9$ and $R^{10}$ is independently selected from hydrido, alkyl, haloalkyl, cycloalkyl, polycycloalkyl, polycycloalkylalkyl, cycloalkylalkyl, aralkyl, aryl, alkenyl, cycloalkenyl, and heterocyclic and heterocyclicalkyl having one or more ring atoms selected from oxygen, sulfur and nitrogen atoms; wherein any of said $R^9$ and $R^{10}$ groups may be substituted at one or more substitutable positions by one or more groups selected from alkyl, halo, haloalkyl and alkoxy; or a pharmaceutically-acceptable salt thereof.

2. Compound of claim 1 wherein m is a number selected from one through five, inclusive; wherein $R^1$ is selected from hydrido, alkyl, hydroxyalkyl, formyl, halo, haloalkyl, cycloalkyl, alkylcycloalkyl, alkylcycloalkyl, cycloalkylalkyl, cycloalkylhaloalkyl, cycloalkylcarbonyl, alkoxy, aralkyl, aralkylhaloalkyl, aryl, haloaryl, aroyl, aryloxy, aryloxyalkyl, aralkoxy, alkoxyalkyl, alkylcarbonyl, alkylcarbonylalkyl, alkoxycarbonyl, cyano, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, alkylsilyloxyalkyl, aryl/alkylsilyloxyalkyl, arylsilyloxyalkyl, mercaptoalkyl, alkoxycarbonyloxy, alkylthio, alkylthioalkyl, alkylsulfinylalkyl, alkylsulfonylalkyl, arylthio, and heterocyclic and heterocyclicalkyl having one or more ring atoms selected from oxygen, sulfur and nitrogen atoms;

wherein each of $R^2$, $R^3$ and $R^4$ is independently selected from hydrido, alkyl, hydroxyalkyl, formyl, halo, haloalkyl, cycloalkyl, alkylcycloalkyl, cycloalkylalkyl, cycloalkylhaloalkyl, cycloalkylcarbonyl, alkoxy, aralkyl, aralkylhaloalkyl, alkoxyalkyl, alkylcarbonyl, alkylcarbonylalkyl, alkylsilyloxyalkyl, alkoxycarbonyl, cyano, nitro, alkylthio, alkylthioalkyl, alkylsulfinylalkyl and alkylsulfonylalkyl;

wherein each of $R^5$, $R^6$, $R^7$ and $R^8$ is independently selected from hydrido, alkyl, hydroxy, hydroxyalkyl, formyl, halo, haloalkyl, cycloalkyl, alkylcycloalkyl, cycloalkylalkyl, cycloalkylhaloalkyl, cycloalkylcarbonyl, alkoxy, aralkyl, aralkylhaloalkyl, aryl, haloaryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, alkylsilyloxyalkyl, alkoxycarbonyloxy, alkylthio, alkylthioalkyl, alkylsulfinylalkyl, alkylsulfonylalkyl and arylthio;

wherein each of $R^1$, $R^2$, $R^3$, $R^4$, $R^5$, $R^6$, $R^7$ and $R^8$ may be further independently selected from amino and amido radicals of the formulae

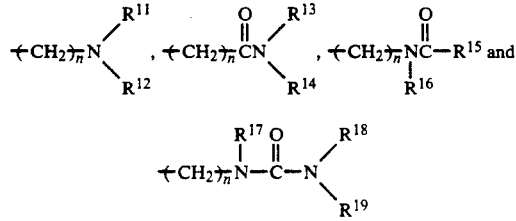

wherein each n is a number independently selected from zero to five, inclusive; wherein each of $R^{11}$ through $R^{19}$ is independently selected from hydrido, alkyl, cycloalkyl, hydroxyalkyl, cycloalkylalkyl, alkoxyalkyl, aralkyl and aryl;
wherein each of $R^9$ and $R^{10}$ is independently selected from hydrido, alkyl, haloalkyl, cycloalkyl, polycycloalkyl, polycycloalkylalkyl, cycloalkylalkyl, aralkyl, aryl, alkenyl, cycloalkenyl, and heterocyclic and heterocyclicalkyl having one or more ring atoms selected from oxygen, sulfur and nitrogen atoms, wherein any of said $R^9$ and $R^{10}$ groups may be substituted at one or more substitutable positions by one or more groups selected from alkyl, halo, haloalkyl and alkoxy; or a pharmaceutically-acceptable salt thereof.

3. Compound of claim 2 wherein m is a number selected from one through four, inclusive; wherein $R^1$ is selected from hydrido, alkyl, hydroxyalkyl, halo, haloalkyl, cycloalkyl, alkylcycloalkyl, cycloalkylalkyl, cycloalkylhaloalkyl, alkoxy, aralkyl, aralkylhaloalkyl, aryl, haloaryl, aryloxy, aryloxyalkyl, alkoxyalkyl, alkylcarbonylalkyl, cyano, carboxyalkyl, alkylcarbonyloxyalkyl, alkoxycarbonylalkyl, aralkoxycarbonylalkyl, aralkylcarbonyloxyalkyl, alkylsilyloxyalkyl, aryl/alkylsilyloxyalkyl, arylsilyloxyalkyl, mercaptoalkyl, alkylthio, alkylthioalkyl, alkylsulfinylalkyl, alkylsulfonylalkyl, arylthio, and heteroaryl and heteroarylalkyl having one or more ring atoms selected from oxygen, sulfur and nitrogen atoms;
  wherein each of $R^2$, $R^3$ and $R^4$ is independently selected from hydrido, alkyl, hydroxyalkyl, halo, haloalkyl, cycloalkyl, alkylcycloalkyl, cycloalkylalkyl, cycloalkylhaloalkyl, alkoxy, aralkyl, aralkylhaloalkyl, alkoxyalkyl, alkylcarbonylalkyl, alkylsilyloxyalkyl, cyano, nitro, alkylthio, alkylthioalkyl, alkylsulfinylalkyl and alkylsulfonylalkyl;
  wherein each of $R^5$, $R^6$, $R^7$ and $R^8$ is independently selected from hydrido, alkyl, hydroxy, hydroxyalkyl, halo, haloalkyl, cycloalkyl, alkylcycloalkyl, cycloalkylalkyl, alkoxy, aralkyl, aryl, haloaryl, aryloxy, aryloxyalkyl, aralkoxy, alkoxyalkyl, cyano, nitro, carboxyl, carboxyalkyl, alkylcarbonyloxy, alkylsilyloxyalkyl, alkoxycarbonyloxy, alkylthio, alkylthioalkyl, alkylsulfinylalkyl, alkylsulfonylalkyl and arylthio;

wherein each of $R^1$, $R^2$, $R^3$, $R^4$, $R^5$, $R^6$, $R^7$ and $R^8$ may be further independently selected from amino and amido radicals of the formulae

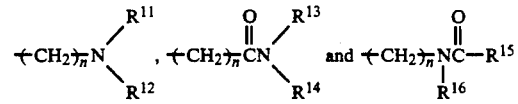

wherein each n is a number independently selected from zero to four, inclusive; wherein each of $R^{11}$ through $R^{16}$ is independently selected from hydrido, alkyl, cycloalkyl, hydroxyalkyl, cycloalkylalkyl, alkoxyalkyl, aralkyl and aryl;
wherein each of $R^9$ and $R^{10}$ is independently selected from hydrido, alkyl, haloalkyl, cycloalkyl, polycycloalkyl, polycycloalkylalkyl, cycloalkylalkyl, aralkyl, aryl, alkenyl, cycloalkenyl, and heterocyclic and heterocyclicalkyl having one or more ring atoms selected from oxygen, sulfur and nitrogen atoms, wherein any of said $R^9$ and $R^{10}$ groups may be substituted at one or more substitutable positions by one or more groups selected from alkyl, halo, haloalkyl and alkoxy, with the proviso that when $R^9$ or $R^{10}$ is an alkenyl or a cycloalkenyl group, then the double bond of such group cannot be adjacent to the nitrogen atom of the amido group of Formula I; or a pharmaceutically-acceptable salt thereof.

4. Compound of claim 3 wherein m is a number selected from one through three, inclusive; wherein $R^1$ is selected from hydrido, alkyl, hydroxyalkyl, halo, haloalkyl, cycloalkyl, alkylcycloalkyl, cycloalkylalkyl, cycloalkylhaloalkyl, alkoxy, phenylalkyl, phenyl, halophenyl, phenoxy, phenoxyalkyl, alkoxyalkyl, cyano, alkylsilyloxyalkyl, phenyl/alkylsilyloxyalkyl, phenylsilyloxyalkyl, alkylthio, phenylthio, and heteroaryl and heteroarylalkyl having one or more ring atoms selected from oxygen, sulfur and nitrogen atoms;
  wherein each of $R^2$, $R^3$ and $R^4$ is independently selected from hydrido, alkyl, hydroxyalkyl, halo, haloalkyl, cycloalkyl, alkylcycloalkyl, cycloalkylalkyl, alkoxy, phenylalkyl, alkoxyalkyl, alkylcarbonylalkyl, alkylsilyloxyalkyl, cyano, nitro and alkylthio; wherein each of $R^5$, $R^6$, $R^7$ and $R^8$ is independently selected from hydrido, alkyl, hydroxy, hydroxyalkyl, halo, haloalkyl, cycloalkyl, alkylcycloalkyl, cycloalkylalkyl, alkoxy, phenylalkyl, phenyl, halophenyl, phenyloxy, phenyloxyalkyl, alkoxyalkyl, cyano, nitro, carboxyalkyl, alkylsilyloxyalkyl, alkylthio and phenylthio;
wherein each of $R^1$, $R^2$, $R^3$, $R^4$, $R^5$, $R^6$, $R^7$ and $R^8$ may be further independently selected from amino and amido radicals of the formulae

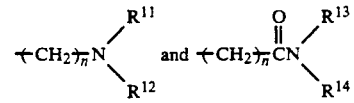

wherein each n is a number independently selected from zero to four, inclusive; wherein each of $R^{11}$ through $R^{14}$ is independently selected from hydrido, alkyl, cycloalkyl, hydroxyalkyl, cycloalkylalkyl, alkoxyalkyl, phenylalkyl and phenyl;

wherein each of $R^9$ and $R^{10}$ is independently selected from hydrido, alkyl, haloalkyl, cycloalkyl, bicycloalkyl, bicycloalkylalkyl, cycloalkylalkyl, phenylalkyl, phenyl, alkenyl, cycloalkenyl, and heterocyclic and heterocyclicalkyl having one or more ring atoms selected from oxygen, sulfur and nitrogen atoms, wherein any of said $R^9$ and $R^{10}$ groups may be substituted at one or more substitutable positions by one or more groups selected from alkyl, halo, haloalkyl and alkoxy, with the proviso that when $R^9$ or $R^{10}$ is an alkenyl or a cycloalkenyl group, then the double bond of such group cannot be adjacent to the nitrogen atom of the amido group of Formula I; or a pharmaceutically-acceptable salt thereof.

5. Compound of claim 4 wherein m is one or two; wherein $R^1$ is selected from hydrido, alkyl, hydroxyalkyl, halo, haloalkyl, cycloalkyl, alkylcycloalkyl, cycloalkylalkyl, cycloalkylhaloalkyl, alkoxy, benzyl, phenyl, halophenyl, alkoxyalkyl, alkylsilyloxyalkyl, phenyl/alkylsilyloxyalkyl, phenylsilyloxyalkyl, alkylthio, furanyl and pyridinyl;

wherein each of $R^2$, $R^3$ and $R^4$ is independently selected from hydrido, alkyl, hydroxyalkyl, halo, haloalkyl, cycloalkyl, alkylcycloalkyl, cycloalkylalkyl, alkoxy, benzyl, alkoxyalkyl, alkylsilyloxyalkyl and alkylthio;

wherein each of $R^5$, $R^6$, $R^7$ and $R^8$ is independently selected from hydrido, alkyl, hydroxy, hydroxyalkyl, formyl, halo, haloalkyl, cycloalkyl, alkylcycloalkyl, cycloalkylalkyl, alkoxy, alkoxyalkyl, alkylsilyloxyalkyl and alkylthio;

wherein each of $R^1$, $R^2$, $R^3$, $R^4$, $R^5$, $R^6$, $R^7$ and $R^8$ may be further independently selected from amino radicals of the formula

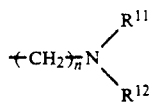

wherein each n is a number independently selected from zero to four, inclusive; wherein each of $R^{11}$ and $R^{12}$ is independently selected from hydrido, alkyl, cycloalkyl, hydroxyalkyl, cycloalkylalkyl, alkoxyalkyl, benzyl and phenyl;

wherein each of $R^9$ and $R^{10}$ is independently selected from hydrido, alkyl, haloalkyl, cycloalkyl, bicycloalkyl, bicycloalkylalkyl, cycloalkylalkyl, phenylalkyl, phenyl, saturated or partially saturated heterocyclicalkyl having 4 to 8 ring atoms, heteroaryl having 5 or 6 ring atoms, alkenyl and cycloalkenyl; wherein any of said $R^9$ and $R^{10}$ groups may be substituted at one or more substitutable positions by one or more groups selected from alkyl, halo, haloalkyl and alkoxy, with the proviso that when $R^9$ or $R^{10}$ is an alkenyl or a cycloalkenyl group, then the double bond of such group cannot be adjacent to the nitrogen atom of the amido group of Formula I; or a pharmaceutically-acceptable salt thereof.

6. Compound of claim 5 wherein m is one; wherein $R^1$ is selected from hydrido, alkyl, hydroxyalkyl, alkoxyalkyl, phenyl, halophenyl, furanyl, pyridinyl, alkylsilyloxyalkyl, amino, monoalkylamino, dialkylamino, aminoalkyl, monoalkylaminoalkyl and dialkylaminoalkyl, wherein when $R^1$ is alkyl or is a group containing alkyl, then such alkyl has one to about six carbon atoms and may have a linear or branched configuration;

wherein each of $R^2$, $R^3$ and $R^4$ is hydrido;

wherein each of $R^5$, $R^6$, $R^7$ and $R^8$ is independently selected from hydrido, hydroxy, alkyl, alkoxy, fluoro, chloro, bromo, haloalkyl, alkylthio, alkoxyalkyl, hydroxyalkyl, alkylthioalkyl, cyano, amino, monoalkylamino, dialkylamino, aminoalkyl, monoalkylaminoalkyl and dialkylaminoalkyl; wherein when any of the foregoing $R^5$, $R^6$, $R^7$ and $R^8$ is alkyl or is a group containing alkyl, such alkyl has one to about six carbon atoms and may have a linear or branched configuration;

wherein each of $R^9$ and $R^{10}$ is independently selected from hydrido, linear or branched chain alkyl having 1 to about 15 carbon atoms, cycloalkyl having 3 to about 8 carbon atoms, bicycloalkyl having 3 to about 8 carbon atoms in each ring, saturated or partially saturated heterocyclicalkyl having 4 to 8 ring atoms, heteroaryl having 5 or 6 ring atoms, phenyl, linear or branched alkenyl having 3 to about 15 carbon atoms with the proviso that the double bond of the alkenyl group cannot be adjacent to the nitrogen, cycloalkenyl having 5 to about 8 carbon atoms with the proviso that the double bond cannot be adjacent to the nitrogen of the amido group of Formula I, and wherein any of said $R^9$ and $R^{10}$ substituents may be further substituted with one or more groups selected from linear or branched lower alkyl, lower alkoxy, chloro and bromo; or a pharmaceutically-acceptable salt thereof.

7. Compound of claim 6 wherein m is one; wherein $R^1$ is selected from hydrido, methyl, ethyl, n-propyl, isopropyl, n-butyl, isobutyl, sec-butyl, tert-butyl, n-pentyl, isopentyl, neopentyl, hexyl, hydroxymethyl, hydroxyethyl, hydroxypropyl, hydroxybutyl, methoxymethyl, ethoxymethyl, propoxymethyl, butoxymethyl, methoxyethyl, methoxypropyl, methoxybutyl, ethoxyethyl, ethoxypropyl, ethoxybutyl, propoxymethyl, propoxyethyl, propoxypropyl, propoxybutyl, butoxymethyl, butoxyethyl, butoxypropyl, butoxybutyl, phenyl, monofluorophenyl, difluorophenyl, monochlorophenyl, dichlorophenyl, monobromophenyl, dibromophenyl, trimethylsilyloxymethyl, trimethylsilyloxyethyl, trimethylsilyloxypropyl, trimethylsilyloxybutyl, triethylsilyloxymethyl, triethylsilyloxyethyl, triethylsilyloxypropyl, triethylsilyloxybutyl, tripropylsilyloxymethyl, tripropylsilyloxyethyl, tripropylsilyloxypropyl, tripropylsilyloxybutyl, tert-butyl(dimethyl)silyloxymethyl, tert-butyl(dimethyl)silyloxyethyl, tert-butyl(dimethyl)silyloxypropyl, tert-butyl(dimethyl)silyloxybutyl, 2-pyridinyl, 3-pyridinyl, amino, N-methylamino, N,N'-dimethylamino, N-ethylamino, N,N'-diethylamino, N-propylamino, N,N'-dipropylamino, N-butylamino, N-N'-dibutylamino, N-methylaminomethyl, N-methylaminoethyl, N-methylaminopropyl, N-methylaminobutyl, N,N'-dimethylaminomethyl, N,N'-dimethylaminoethyl, N,N'-dimethylaminopropyl, N,N'-dimethylaminobutyl, N,N'-diethylaminomethyl, N,N'-diethylaminoethyl, N,N'-diethylaminopropyl, N,N'-diethylaminobutyl, N,N'-dipropylaminomethyl, N,N'-dipropylaminoethyl, N,N'-dipropylaminopropyl, N,N'-dipropylaminobutyl-, N,N'-dibutylaminomethyl, N,N'-dibutylaminoethyl, N,N'-dibutylaminopropyl and N,N'-dibutylaminobutyl, wherein when R¹ is alkyl group or is one of the foregoing groups containing an alkyl group, such alkyl group may be linear or branched in configuration;

wherein each of R², R³ and R⁴ is hydrido;

wherein each of R⁵, R⁶, R⁷ and R⁸ is independently selected from hydrido, methyl, ethyl, n-propyl, isopropyl, n-butyl, isobutyl, sec-butyl, tert-butyl, n-pentyl, isopentyl, neopentyl, hexyl, fluoro, chloro, bromo, hydroxy, methoxy, ethoxy, propoxy, butoxy, pentoxy, trifluoromethyl, perfluoroethyl, dichloromethyl, methylthio, ethylthio, propylthio, butylthio, pentylthio, hydroxymethyl, hydroxyethyl, hydroxypropyl, hydroxybutyl, methoxymethyl, ethoxymethyl, propoxymethyl, butoxymethyl, methoxyethyl, methoxypropyl, methoxybutyl, ethoxyethyl, ethoxypropyl, ethoxybutyl, propoxymethyl, propoxyethyl, propoxypropyl, propoxybutyl, butoxymethyl, butoxyethyl, butoxypropyl, butoxybutyl, methylthiomethyl, methylthioethyl, methylthiopropyl, methylthiobutyl, ethylthiomethyl, ethylthioethyl, ethylthiopropyl, ethylthiobutyl, propylthiomethyl, propylthioethyl, propylthiopropyl, propylthiobutyl, butylthiomethyl, butylthioethyl, butylthiopropyl, butylthiobutyl, cyano, amino, N-methylamino, N,N'-dimethylamino, N-ethylamino, N,N'-diethylamino, N-propylamino, N,N'-dipropylamino, N-butylamino, N-N'-dibutylamino, N-methylaminomethyl, N-methylaminoethyl, N-methylaminopropyl, N-methylaminobutyl, N,N'-dimethylaminomethyl, N,N'-dimethylaminoethyl, N,N'-dimethylaminopropyl, N,N'-dimethylaminobutyl, N,N'-diethylaminomethyl, N,N'-diethylaminoethyl, N,N'-diethylaminopropyl, N,N'-diethylaminobutyl, N,N'-dipropylaminomethyl, N,N'-dipropylaminoethyl, N,N'-dipropylaminopropyl, N,N'-dipropylaminobutyl, N,N'-dibutylaminomethyl, N,N'-dibutylaminoethyl, N,N'-dibutylaminopropyl and N,N'-dibutylaminobutyl; wherein when any of R⁵, R⁶, R⁷ and R⁸ is alkyl or is a group containing alkyl, such alkyl group may be linear or branched in configuration; wherein each of R⁹ and R¹⁰ is independently selected from hydrido, methyl, ethyl, n-propyl, isopropyl, isobutyl, sec-butyl, tert-butyl, n-pentyl, isopentyl, neopentyl, n-hexyl, n-heptyl, n-octyl, n-nonyl, n-decyl, 1,1,3,3-tetramethylbutyl, 2,2-dimethylethyl, 1,1-diethylmethyl, cyclopropyl, cyclobutyl, cyclohexyl, cycloheptyl, cyclooctyl, methylcyclopentyl, ethylcyclopentyl, 2-methylcyclohexyl, 3-methylcyclohexyl, 4-methylcyclohexyl, 3,5-dimethylcyclohexyl, ethylcyclohexyl, 3,5-diethylcyclohexyl, norbornyl, decalin, 2,2,1-bicycloheptyl, 2,2,1-bicycloheptylmethyl, phenyl, furanyl, pyranyl, oxetanyl, pyrrolidinyl, piperidinyl, tetrahydrothiophenyl, thiopyranyl, morpholino, piperazinyl, furanylmethyl, pyranylmethyl, oxetanylmethyl, pyrrolidinylmethyl, piperidinylmethyl, tetrahydrothiophenylmethyl, thiopyranylmethyl, morpholinomethyl, piperazinylmethyl, pyrrole, pyrrolemethyl, pyrazole, pyrazolemethyl, imidazole, imidazolemethyl, triazole, triazolemethyl, tetrazole, tetrazolemethyl, thiazole, thiazolemethyl, oxazole, oxazolemethyl, pyrazinyl, pyrazinylmethyl, 2-pyridinyl, 2-pyridinylmethyl, 3-pyridinyl and 3-pyridinylmethyl; or a pharmaceutically-acceptable salt thereof.

8. Compound of claim 7 selected from compounds, and their pharmaceutically-acceptable salts, of the group of compounds consisting of N,N-dicyclopentyl-4-(4H-imidazo[4,5-b]pyridin-4-ylmethyl)-3-methoxybenzamide;

N cyclohexyl-4-(4H-imidazo[4,5-b]pyridin-4-ylmethyl)-2-methoxy-N-(1-methylethyl)benzamide;

N-cyclohexyl-4-(4H-imidazo[4,5-b]pyridin-4-ylmethyl)-3-methoxy-N-(1 methylethyl)benzamide;

N-cyclopentyl-N-(3,5-dimethylcyclohexyl)-4-(4H-imidazo[4,5-b]pyridin-4-ylmethyl)-2-methoxybenzamide N-cyclohexyl-3-methoxy-N-(1-methylethyl)-4-[(2-methyl-4H-imidazo[4,5-b]pyridin-4-yl]methyl]benzamide;

N-cyclohexyl-4-[[2-(hydroxymethyl)-4H-imidazo[4,5-b]pyridin-4-yl]methyl]-3-methoxy-N-(1-methylethyl)benzamide;

N-cyclohexyl-3-methoxy-N-(1-methylethyl)-4-[[2-(2-pyridinyl)-4H-imidazo[4,5-b]pyridin-4-yl]methyl]-benzamide;

N-cyclohexyl-3-methoxy-N-(1-methylethyl)-4-[[2-(3-pyridinyl)-4H-imidazo[4,5-b]pyridin-4-yl]methyl]-benzamide; and N-cyclohexyl-4-(4H-imidazo[4,5-b]pyridin-4-ylmethyl)-N-(1-methylethyl)benzamide.

9. Compound of claim 8 which is N,N-dicyclopentyl-4-(4H-imidazo[4,5-b]pyridin-4-ylmethyl)-3-methoxybenzamide or a pharmaceutically-acceptable salt thereof.

10. Compound of claim 8 which is N-cyclohexyl-4-(4H-imidazo[4,5-b]pyridin-4-ylmethyl)-2-methoxy-N-(1-methylethyl)benzamide or a pharmaceutically-acceptable salt thereof.

11. Compound of claim 8 which is N-cyclohexyl-4-(4H-imidazo[4,5-b]pyridin-4-ylmethyl)-3-methoxy-N-(1-methylethyl)benzamide or a pharmaceutically-acceptable salt thereof.

12. Compound of claim 8 which is N-cyclopentyl-N-(3,5-dimethylcyclohexyl)-4-(4H-imidazo[4,5-b]pyridin-4-ylmethyl)-2-methoxybenzamide or a pharmaceutically-acceptable salt thereof.

13. Compound of claim 8 which is N-cyclohexyl-3-methoxy-N-(1-methylethyl)-4-[(2-methyl-4H-imidazo[4,5-b]pyridin-4-yl]methyl]benzmide or a pharmaceutically-acceptable salt thereof.

14. Compound of claim 8 which is N-cyclohexyl-4-[[2-(hydroxymethyl)-4H-imidazo[4,5-b]pyridin-4-yl]methyl]-3-methoxy N-(1-methylethyl)benzamide or a pharmaceutically-acceptable salt thereof.

15. Compound of claim 8 which is N-cyclohexyl-3-methoxy-N-(1 methylethyl)-4-[[2-(2-pyridinyl)-4H-imidazo[4,5-b]pyridin-4-yl]methyl]benzamide or a pharmaceutically-acceptable salt thereof.

16. Compound of claim 8 which is N-cyclohexyl-imidazo[4,5-b]pyridin-4-yl]methyl]benzamide or a pharmaceutically-acceptable salt thereof.

17. Compound of claim 8 which is N-cyclohexyl-4-(4H-imidazo[4,5-b]pyridin-4-ylmethyl)-N-(1-methylethyl)benzamide or a pharmaceutically-acceptable salt thereof.

18. A pharmaceutical composition comprising at least one pharmaceutically-acceptable carrier or diluent and a PAF-antagonist-mediating therapeutically-effective amount of an active compound selected from compounds of Formula I of claim 1.

19. A method for treating a disease mediated by platelet activating factor, said method comprising administering to a subject susceptible to or afflicted with said disease, a therapeutically-effective amount of a compound of Formula I of claim 1.

20. The method of claim 19 wherein said disease is an inflammatory disease.

* * * * *